United States Patent
Pandya et al.

(10) Patent No.: US 8,227,492 B2
(45) Date of Patent: Jul. 24, 2012

(54) SULFOXAMINE DERIVATIVES AS FACTOR XA INHIBITORS

(75) Inventors: Vrajesh B. Pandya, Ahmedadabad (IN); Pankaj Ramanbhai Patel, Ahmedadabad (IN)

(73) Assignee: Cadila Healthcare Limited, Ahmedadabad (IN)

( * ) Notice: Subject to any disclaimer, the term of this patent is extended or adjusted under 35 U.S.C. 154(b) by 103 days.

(21) Appl. No.: 12/671,935

(22) PCT Filed: Aug. 4, 2008

(86) PCT No.: PCT/IN2008/000483
§ 371 (c)(1),
(2), (4) Date: Apr. 12, 2010

(87) PCT Pub. No.: WO2009/053999
PCT Pub. Date: Apr. 30, 2009

(65) Prior Publication Data
US 2011/0065717 A1    Mar. 17, 2011

(30) Foreign Application Priority Data

| Aug. 7, 2007 | (IN) | 1525/MUM/2007 |
| Sep. 24, 2007 | (IN) | 1852/MUM/2007 |
| Oct. 15, 2007 | (IN) | 2047/MUM/2007 |

(51) Int. Cl.
*A61K 31/44* (2006.01)
*C07D 213/72* (2006.01)
(52) U.S. Cl. ........... 514/352; 546/304
(58) Field of Classification Search ........... 514/352; 546/304
See application file for complete search history.

(56) References Cited

U.S. PATENT DOCUMENTS

| 5,576,343 A | 11/1996 | Nagahara et al. |
| 5,691,364 A | 11/1997 | Buckman et al. |
| 6,140,351 A | 10/2000 | Arnaiz et al. |
| 7,087,609 B2 * | 8/2006 | Wu et al. ........... 514/253.01 |
| 7,799,782 B2 * | 9/2010 | Munson et al. ........... 514/234.5 |

FOREIGN PATENT DOCUMENTS

| WO | WO99/00121 | 1/1999 |
| WO | WO01/19788 A | 3/2001 |
| WO | WO2004/026816 A1 | 4/2004 |

OTHER PUBLICATIONS

Vu et al., "Molecular Cloning of a Functional Thrombin Receptor Reveals a Novel Proteolytic Mechanism of Receptor Activation" Cell 64(6): 1057-68 (1991).
Montalbetti et al., "Amide Bond Formation and Peptide Coupling", Tetrahedron 61(46): 10827-10852 (2005).
Igarashi et al., "Synthesis and Evaluation of Carbamate Prodrugs of a Phenolic Compound", Chem. Pharm. Bull. 55(2): 328-333 (2007).
Zhang et al., "Design, Synthesis, and SAR of Anthranilamide-based Factor Xa Inhibitors Incorporating Substituted Biphenyl P4 Motifs", Bioorganic & Medicinal Chemistry Letters, 14:983-987 (2004).
International Search Report issued in counterpart PCT Appln No. PCT/IN2008/000483, 2008.
Written Opinion issued in counterpart PCT Appln No. PCT/IN2008/000483, 2008.
International Preliminary Report on Patentability issued in counterpart PCT Appln No. PCT/IN2008/000483, 2008.

* cited by examiner

*Primary Examiner* — Rei-tsang Shiao
(74) *Attorney, Agent, or Firm* — IpHorgan Ltd.

(57) ABSTRACT

The present invention relates to novel substituted sulfoximine derivatives of the general formula (I), their tautomeric forms, their stereoisomers, their pharmaceutically acceptable salts, pharmaceutical compositions containing them, methods for their preparation, use of these compounds in medicine and the intermediates involved in their preparation.

16 Claims, No Drawings

SULFOXAMINE DERIVATIVES AS FACTOR XA INHIBITORS

CROSS-REFERENCE TO RELATED APPLICATIONS

This is a Section 371 National Stage application based on PCT International Application No. PCT/IN2008/000483, filed on Aug. 4, 2008, claiming priority from Indian Patent Application No. 1525/MUM/2007 filed on Aug. 7, 2007, 1852/MUM/2007 filed on Sep. 24, 2007, and 2047/MUM/2007 filed on Oct. 15, 2007, the contents of each application hereby being incorporated by reference.

FIELD OF INVENTION

The present invention relates to novel substituted sulfoximine derivatives of the general formula (I), their tautomeric forms, their stereoisomers, their pharmaceutically acceptable salts, pharmaceutical compositions containing them, methods for their preparation, use of these compounds in medicine and the intermediates involved in their preparation.

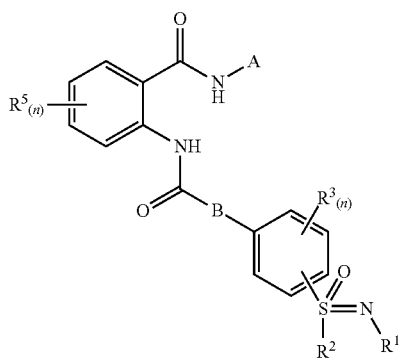

(I)

BACKGROUND OF THE INVENTION

Factor Xa is a member of the trypsin-like serine protease class of enzymes. A one-to-one binding of factors Xa and Va with calcium ions and phospholipid forms the prothrombinase complex, which converts prothrombin to thrombin. Thrombin, in turn, converts fibrinogen to fibrin, which polymerizes to form insoluble fibrin. Factor Xa can be activated by two distinct complexes, by tissue factor-VIIa complex on the "Xa burst" pathway and by the factor IXa-VIIIA complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Therefore, the coagulation cascade is naturally regulated by factor Xa.

The primary advantage of inhibiting factor Xa over thrombin in order to prevent coagulation is the focal role of factor Xa versus the multiple functions of thrombin. Thrombin not only catalyzes the conversion of fibrinogen to fibrin, factor VIII to VIIIA, factor V to Va, and factor XI to XIa, but also activates platelets, is a monocyte chemotactic factor, and mitogen for lymphocytes and smooth muscle cells. Thrombin activates protein C, the in vivo anti-coagulant inactivator of factors Va and VIIIa, when bound to thrombomodulin. In circulation, thrombin is rapidly inactivated by antithrombin III (ATIII) and heparin cofactor II (HCII) in a reaction which is catalyzed by heparin or other proteolycan-associated glycosaminoglycans, whereas thrombin in tissues is inactivated by the protease, nexin. Thrombin carries out its multiple cellular activation functions through a unique "tethered ligand" thrombin receptor (Cell 1991; 64: 1057), which requires the same anionic binding site and active site used in fibrinogen binding and cleavage and by thrombomodulin binding and protein C activation. Thus, a diverse group of in vivo molecular targets compete to bind thrombin and the subsequent proteolytic events will have very different physiological consequences depending upon which cell type and which receptor, modulator, substrate or inhibitor binds thrombin.

U.S. Pat. No. 5,576,343 describes aromatic amidine derivatives as anticoagulants and also as inhibitors of Factor Xa. U.S. Pat. No. 5,691,364 describes benzamidine derivatives as anti-coagulants.

WO9900121 describes 1,2-diamino compounds as inhibitors of Factor Xa. U.S. Pat. No. 6,140,351 describes ortho anthranilamide derivatives as anticoagulants. WO2004026816 describes aromatic benzoate derivatives as Liver X-receptor modulators. WO0119788 describes benzamide and related inhibitors of Factor Xa However, the therapeutic potential of these compounds to treat diseases has not yet been proved and so there remains the need to develop newer medicines which are better or of comparable efficacy with the present treatment regimes, have lesser side effects and require a lower dosage regime We herein disclose novel compounds of formula (I) which shows a strong anticoagulant effect through its highly specific and reversible FXa-inhibiting activity and is useful as a drug for the prevention and treatment of various thrombosis- and embolism-based diseases The inventive compounds of the present invention have a high anticoagulant capacity based on its excellent FXa inhibition activity. The invention also relates to an anticoagulant, or a thrombosis- or embolism preventing or treating agent that contains the sulfoximine derivative or a salt thereof of the present invention as an active ingredient. This invention is also directed to pharmaceutical compositions containing the compounds of the invention and methods of using the compounds to treat disease-states characterized by thrombotic activity.

SUMMARY OF THE INVENTION

The present invention discloses novel compounds as defined by the general formula (I) that are factor Xa inhibitors and are useful for the prevention and treatment of thrombin-related disorders. The compounds of the present invention are useful in the treatment of human and/or animal body by inhibition of factor Xa. The compounds of this invention are therefore suitable for the prevention and treatment of disease states that are characterized by thrombin activity.

OBJECTS OF THE INVENTION

An important object of the present invention is to provide novel substituted sulfoximine derivatives represented by the general formula (I), their tautomeric forms, their stereoisomers, their pharmaceutically acceptable salts, and pharmaceutical compositions containing them or their mixtures thereof.

Another object of the present invention is provided a process for the preparation of novel substituted sulfoximine derivatives represented by the general formula (I), their tautomeric forms, their stereoisomers, their pharmaceutically acceptable salts.

Another object of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

DESCRIPTION OF THE INVENTION

Accordingly, the present invention relates to compounds of the general formula (I),

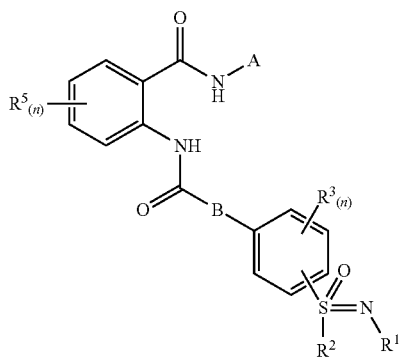

(I)

wherein

'A' represents optionally substituted carbocyclic or heterocyclic groups;

substituents on 'A' may be selected from halogen, hydrogen, hydroxy, optionally substituted amino, nitro, alkylamino, aminoalkyl, $(C_1-C_6)$alkyl, halo$(C_1-C_6)$alkyl, $(C_1-C_6)$alkoxy, aminocarbonyl, aminosulfonyl, and optionally substituted aminooxy derivatives;

'B' represents either a bond so that carbonyl group can be directly linked to the phenyl ring having sulfoximide moiety, or B represents a radical of following formula

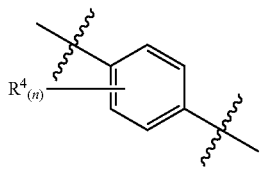

$R^2$ represents $(C_1-C_{10})$alkyl, $(C_3-C_{10})$cycloalkyl groups, wherein the $(C_1-C_{10})$alkyl chain may further optionally contain from 1-3 heteroatoms selected from $NR_aR_b$, O, S or the groups carbonyl or iminocarbonyl; wherein either of $R_aR_b$ if present, is independently selected from H, $(C_1-C_3)$ alkyl groups; provided that the chain forms other than S—S, S—O, or O—O bond;

the $(C_1-C_{10})$alkyl group may be optionally substituted with hydrogen, hydroxyl, amino, $(C_1-C_6)$alkoxy, acyl, acylamino, alkylamino, aminoalkyl, mono, di or trisubstituted amino, alkylsulfonylamino, alkoxycarbonylamino, aminocarbonylamino, heterocycle, alkylsulfonyl, aminocarbonyl derivatives;

the $(C_3-C_{10})$ cycloalkyl group may be optionally substituted with hydrogen, hydroxyl, amino, $(C_1-C_6)$ alkoxy, acyl, acylamino, alkylamino, aminoalkyl, mono, di or trisubstituted amino, alkylsulfonylamino, alkoxycarbonylamino, aminocarbonylamino, heterocycle, alkylsulfonyl, aminocarbonyl derivatives;

$R^1$ represents hydrogen, cyano or the groups selected from
optionally substituted $(C_1-C_{10})$alkyl groups wherein the alkyl group may optionally contain from 1-3 heteroatoms selected from $NR_aR_b$, O, S or the groups carbonyl or iminocarbonyl; wherein either of RaRb if present, is independently selected from H, $(C_1-C_3)$alkyl groups; provided that the chain forms other than S—S, S—O, or O—O bond; or $R^1$ represents
optionally substituted groups selected from $(C_3-C_{10})$ cycloalkyl, halo$(C_1-C_6)$alkyl, $(C_1-C_6)$heteroaryl, $(C_1-C_6)$aryl, aralkyl, heterocycle, heteroarylalkyl, heterocyclylalkyl, acyl, aminoalkyl, hydroxyalkyl, alkoxyalkyl, aryloxyalkyl, aralkoxyalkyl, aminocarbonyl, alkoxycarbonyl, cycloalkylcarbonyl, heterocyclylcarbonyl, arylcarbonyl, aminosulfonyl and alkylsulfonyl derivatives;

or $R^1$ represents the following groups,

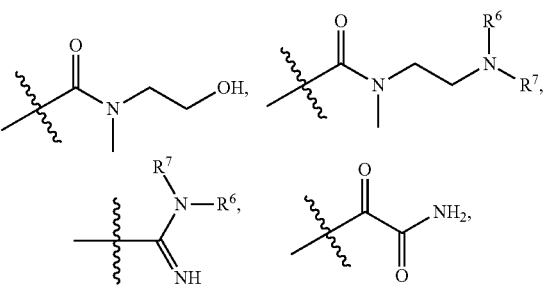

where, $R^6$ and $R^7$ are independently selected from hydrogen, $(C_1-C_6)$alkyl; alternatively, $R^6$ and $R^7$ may cyclise to form a 5-7 membered heterocyclic ring.

The suitable substituents on $R^1$ may be selected from hydrogen, $(C_1-C_6)$alkyl, halogen, cyano, optionally substituted mono, di or trisubstituted amino, optionally substituted groups selected from carbocyclic or heterocyclic, $(C_1-C_6)$ alkoxy, alkylsulfonyl, aminosulfonyl groups;

$R^3$, $R^4$ and $R^5$ may be same or different and at each occurrence independently represents hydrogen, hydroxyl, halo, thio, amino, nitro, or substituted or unsubstituted groups selected from $(C_1-C_6)$alkyl, $(C_1-C_6)$cycloalkyl, halo$(C_1-C_6)$alkyl, $(C_1-C_6)$alkoxy, heterocycleoxy, halo$(C_1-C_6)$alkoxy, alkylamino, aminoalkyl, mono, di or trisubstituted amino, hydroxyalkyl, alkoxyalkyl, alkylsulfonyl, alkylsulfonylamino, aminocarbonyl, and aminosulfonyl derivatives; In a still further embodiment, when any of $R^3$, $R^4$ and $R^5$ represents $(C_1-C_6)$alkoxy group, such $(C_1-C_6)$alkoxy group is further substituted with mono, di or tri substituted amino or a heterocyclic groups;

n represents integers from 1-4.

In a further embodiment, preferred substituents on A may be selected from halogen, hydroxy, optionally substituted amino, aminoalkyl, $(C_1-C_6)$ alkoxy, aminocarbonyl groups; preferred substituents on $R^2$ may be selected from hydrogen, hydroxyl, mono, di or trisubstituted amino, $(C_1-C_6)$alkoxy groups;

Preferred $R^1$ groups may be selected from hydrogen, cyano, optionally substituted groups selected from acyl, aminocarbonyl, $(C_1-C_{10})$ alkyl, aminoalkyl, hydroxyalkyl, heterocycle, heterocyclylalkyl groups;

Preferred substituents on $R^1$ may be selected from hydrogen, halogen, cyano, optionally substituted groups selected from $(C_1-C_6)$alkyl, $(C_1-C_6)$alkoxy, mono, di or trisubstituted amino, carbocyclic or heterocyclic groups;.

Preferred $R^3$, $R^4$, $R^5$ groups may be selected from hydrogen, hydroxyl, halo, optionally substituted $(C_1-C_6)$alkyl, $(C_1-C_6)$alkoxy, heterocycleoxy, mono, di or trisubstituted amino groups.

In a further embodiment the groups, radicals described above may be selected from:

- the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;
- the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like;
- the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;
- the "haloalkyl" group is selected from an alkyl radical, as defined above, suitably substituted with one or more halogens; such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;
- the "haloalkoxy" group is selected from suitable haloalkyl, as defined above, directly attached to an oxygen atom, more preferably groups selected from fluoromethoxy, chloromethoxy, fluoroethoxy, chloroethoxy and the like;
- the "aryl" or "aromatic" group used either alone or in combination with other radicals, is selected from a suitable aromatic system containing one, two, or three rings wherein such rings may be attached together in a pendant manner or may be fused, more preferably the groups are selected from phenyl, naphthyl, tetrahydronaphthyl, indane, biphenyl, and the like;
- the "heterocyclyl" or "heterocyclic" group used either alone or in combination with other radicals, is selected from suitable saturated, partially saturated or unsaturated aromatic or non aromatic mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl, and the like; In one embodiment, the heterocycle group, wherever applicable, may consists of appropriate number of carbon atoms and include from 1-4 heteroatoms selected from the group consisting of N, O, and $S(O)p$, p=0-2, wherein the heterocycle may further be substituted with 1-2 carbonyl or 1-2 iminocarbonyl groups or one or more groups selected from $R^8$ wherein $R^8$ is selected from H, hydroxyl, halogen, cyano, optionally substituted groups selected from $(C_1-C_6)$alkyl, alkoxy, amino, mono, di or trisubstituted amino, hydroxyalkyl, aminoalkyl, heterocyclylalkyl, aminocarbonyl groups;

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclo decane (decalin), [2.2.2]bicyclooctane, fluorenyl, phenyl, naphthyl, indanyl, adamantyl, or tetrahydronaphthyl (tetralin);

- the "heteroaryl" or "heteroaromatic" group used either alone or in combination with other radicals, is selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;
- the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom;
- the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;
- the "mono-substituted amino" group used either alone or in combination with other radicals, represents an amino group substituted with one group selected from $(C_1-C_6)$ alkyl, substituted alkyl, aryl, substituted aryl or arylalkyl groups as defined earlier, more preferably such groups are selected from methylamine, ethylamine, n-propylamine, n-butylamine, n-pentylamine and the like;
- the "disubstituted amino" group used either alone or in combination with other radicals, represents an amino group, substituted with two radicals that may be same or different selected from $(C_1-C_6)$alkyl, substituted alkyl, aryl, substituted aryl, or arylalkyl groups, as defined above, more preferably the groups are selected from dimethylamino, methylethylamino, diethylamino, phenylmethyl amino and the like;
- the "alkylamino" used either alone or in combination with other radicals, represents an alkyl group, as defined above, linked through amino having a free valence bond from the nitrogen atom such as methyl amino, ethyl amino and the like;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "aminocarbonylamino", "dialkgroups used alone or in combination with other radicals, is a carbonylamino ($-CONH_2$) group, attached to amino($NH_2$), alkylamino group or dialkylamino group respectively, where alkyl group is as defined above;

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonyl" group used either alone or in combination with other radicals, may be selected from "aminocarbonyl", "aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted;

the "aminosulfonyl" group used either alone or in combination with other radicals, may be selected from "aminosulfonyl", "aminosulfonylalkyl", "n-alkylaminosulfonyl", "N-arylaminosulfonyl", "N,N-dialkylaminosulfonyl", "N-alkyl-N-arylaminosulfonyl", "N-alkyl-N-hydroxyaminosulfonyl", and "N-alkyl-N-hydroxyaminosulfonylalkyl", each of them being optionally substituted.

the "sulfonyl" group or "sulfones derivatives" used either alone or in combination with other radicals, with other terms such as alkylsulfonyl, represents a divalent radical $-SO_2-$, or $R_xSO_2-$, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like;

the term "aminooxy" represents an amino group as defined above attached to an oxygen atom, such that oxygen acts as the point of attachement.

Suitable groups and substituents on the groups may be selected from those described anywhere in the specification. Preferred compounds according to the present invention include but not limited to:

S-[4-(N-{2-[N-(5-chloro(2-pyridyl))carbamoyl]-4-chlorophenyl}carbamoyl)phenyl]-S-methyl sulfoximide;

S-[4-(N-{2-[N-(5-chloro(2-pyridyl))carbamoyl]-4-methoxyphenyl}carbamoyl)phenyl]-S-methyl sulfoximide;

S-[4-(N-{2-[N-(5-chloro(2-pyridyl))carbamoyl]-4-chlorophenyl}carbamoyl)phenyl]-S-ethyl sulfoximide;

S-[4-(N-{2-[N-(5-chloro(2-pyridyl))carbamoyl]-4-chlorophenyl}carbamoyl)phenyl]-S-methyl-N-chloroacetyl sulfoximide;

S-[4-(N-{2-[N-(5-chloro(2-pyridyl))carbamoyl]-4-chlorophenyl}carbamoyl)phenyl]-S-methyl-N-acetyl sulfoximide;

S-[4-(N-{2-[N-(5-chloro(2-pyridyl))carbamoyl]-4-chlorophenyl}carbamoyl)phenyl]-S-methyl-N-propionyl sulfoximide;

S-[4-(N-{2-[N-(5-chloro(2-pyridyl))carbamoyl]-4-chlorophenyl}carbamoyl)phenyl]-S-methyl-N-cyclopropylcarbonyl sulfoximide;

S-[4-(N-{2-[N-(5-chloro(2-pyridyl))carbamoyl]-4-chlorophenyl}carbamoyl)phenyl]-S-methyl-N-methoxycarbonyl sulfoximide;

S-[4-(N-{2-[N-(5-chloro(2-pyridyl))carbamoyl]-4-chlorophenyl}carbamoyl)phenyl]-S-methyl-N-methanesulfonyl sulfoximide;

S-[4-(N-{2-[N-(5-chloro(2-pyridyl))carbamoyl]-4-chlorophenyl}carbamoyl)phenyl]-S-methyl-N-cyano sulfoximide;

S-[4-(N-{2-[N-(5-chloro(2-pyridyl))carbamoyl]-4-chlorophenyl}carbamoyl)phenyl]-S-methyl-N-carbamoyl sulfoximide;

S-[4-(N-{2-[N-(5-chloro(2-pyridyl))carbamoyl]-4-chlorophenyl}carbamoyl)phenyl]-S-methyl-N-(tert-butoxycarbonylamino-acetyl) sulfoximide;

S-[4-(N-{2-[N-(5-chloro(2-pyridyl))carbamoyl]-4-chlorophenyl}carbamoyl)phenyl]-S-methyl-N-aminocarbonylcarbonyl sulfoximide;

S-[4-(N-{2-[N-(5-chloro(2-pyridyl))carbamoyl]-4-chlorophenyl}carbamoyl)phenyl]-S-methyl-N-(4-pyridylcarbonyl)sulfoximide;

S-[4-(N-{2-[N-(5-chloro(2-pyridyl))carbamoyl]-4-chlorophenyl}carbamoyl)phenyl]-S-methyl-N-(4-piperidinylcarbonyl)sulfoximide;

S-[4-(N-{2-[N-(5-chloro(2-pyridyl))carbamoyl]-4-chlorophenyl}carbamoyl)phenyl]-S-methyl-N-(1-Ethyl-piperidine-4-carbonyl)sulfoximide;

S-[4-(N-{2-[N-(5-chloro(2-pyridyl))carbamoyl]-4-chlorophenyl}carbamoyl)phenyl]-S-methyl-N-(1-acetyl-piperidine-4-carbonyl)sulfoximide;

S-[4-(N-{2-[N-(5-chloro(2-pyridyl))carbamoyl]-4-chlorophenyl}carbamoyl)phenyl]-S-methyl-N-cyanoacetyl sulfoximide;

S-[4-(N-{2-[N-(5-chloro(2-pyridyl))carbamoyl]-4-chlorophenyl}carbamoyl)phenyl]-S-methyl-N-methoxyacetyl sulfoximide;

S-[4-(N-{2-[N-(5-chloro(2-pyridyl))carbamoyl]-4-methoxyphenyl}carbamoyl)phenyl]-S-methyl-N-methoxyacetyl sulfoximide;

S-[4-(N-{2-[N-(5-chloro(2-pyridyl))carbamoyl]-4-chlorophenyl}carbamoyl)phenyl]-S-ethyl-N-methoxyacetyl sulfoximide;

S-[4-(N-{2-[N-(5-chloro(2-pyridyl))carbamoyl]-4-chlorophenyl}carbamoyl)phenyl]-S-methyl-N-ethoxyacetyl sulfoximide;

S-[4-(N-{2-[N-(5-chloro(2-pyridyl))carbamoyl]-4-chlorophenyl}carbamoyl)phenyl]-S-methyl-N-(acetylamino-acetyl)sulfoximide;

S-[4-(N-{2-[N-(5-chloro(2-pyridyl)) carbamoyl]-4-chlorophenyl}carbamoyl)phenyl]-S-methyl-N-[2-(4-pyridylthio)-acetyl]sulfoximide;

S-[4-(N-{2-[N-(5-chloro(2-pyridyl))carbamoyl]-4-chlorophenyl}carbamoyl)phenyl]-S-methyl-N-(2-dimethylamino-acetyl)sulfoximide;

S-[4-(N-{2-[N-(5-chloro(2-pyridyl))carbamoyl]-4-methoxyphenyl}carbamoyl)phenyl]-S-methyl-N-(2-dimethylamino-acetyl)sulfoximide;

S-[4-(N-{2-[N-(5-chloro(2-pyridyl))carbamoyl]-4-chlorophenyl}carbamoyl)phenyl]-S-methyl-N-(2-diethylamino-acetyl)sulfoximide;

S-[4-(N-{2-[N-(5-chloro(2-pyridyl))carbamoyl]-4-methoxyphenyl}carbamoyl)phenyl]-S-methyl-N-(2-diethylamino-acetyl)sulfoximide;

S-[4-(N-{2-[N-(5-chloro(2-pyridyl))carbamoyl]-4-chlorophenyl}carbamoyl)phenyl]-S-methyl-N-[2-(Methyl-propyl-amino)acetyl]sulfoximide;

S-[4-(N-{2-[N-(5-chloro(2-pyridyl))carbamoyl]-4-chlorophenyl}carbamoyl)phenyl]-S-methyl-N-(2-diisopropylamino-acetyl)sulfoximide;

S-[4-(N-{2-[N-(5-chloro(2-pyridyl))carbamoyl]-4-chlorophenyl}carbamoyl)phenyl]-S-methyl-N-[2-(Carbamoylmethyl-methyl-amino)-acetyl]sulfoximide;

S-[4-(N-{2-[N-(5-chloro(2-pyridyl))carbamoyl]-4-chlorophenyl}carbamoyl)phenyl]-S-methyl-N-[(2-Pyrrolidin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[(2-Piperidin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-hydroxypiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-aminopiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-carbamoylpiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-morpholinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-methyl-piperazinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-methyl-homopiperazinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(Piperazin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(3-Oxo-piperazin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(Imidazol-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(1,2,4 Triazol-1-yl)-acetyl]sulfoximide;

S-[4-(N-{2-[N-(5-chloro(2-pyridyl))carbamoyl]-4-chlorophenyl}carbamoyl)phenyl]-S-methyl-N-[(N-methoxy-N-methyl)-carbamoyl]sulfoximide;

S-[4-(N-{2-[N-(5-chloro(2-pyridyl))carbamoyl]-4-chlorophenyl}carbamoyl)phenyl]-S-methyl-N-[(N-hydroxy-N-methyl)-carbamoyl]sulfoximide;

S-[4-(N-{2-[N-(5-chloro(2-pyridyl))carbamoyl]-4-chlorophenyl}carbamoyl)phenyl]-S-methyl-N-[(2-Hydroxy-ethyl)-methyl-carbamoyl]sulfoximide;

S-[4-(N-{2-[N-(5-chloro(2-pyridyl))carbamoyl]-4-chlorophenyl}carbamoyl)phenyl]-S-methyl-N-[(4-methylpiperazin-1-yl)-carbonyl]sulfoximide;

S-[4-(N-{2-[N-(5-chloro(2-pyridyl))carbamoyl]-4-chlorophenyl}carbamoyl)phenyl]-S-methyl-N-(carbamoylmethyl)sulfoximide;

S-[4-(N-{2-[N-(5-chloro(2-pyridyl))carbamoyl]-4-chlorophenyl}carbamoyl)phenyl]-S-methyl-N-[2-hydroxy-ethyl]sulfoximide;

S-[4-(N-{2-[N-(5-chloro(2-pyridyl))carbamoyl]-4-chlorophenyl}carbamoyl)phenyl]-S-methyl-N-(2-(diethylamino)ethyl)sulfoximide;

S-[4-(N-{2-[N-(5-chloro(2-pyridyl))carbamoyl]-4-chlorophenyl}carbamoyl)phenyl]-S-methyl-N-(2-(pyrrolidin-1-yl)ethyl)sulfoximide;

S-[4-(N-{2-[N-(5-chloro(2-pyridyl))carbamoyl]-4-chlorophenyl}carbamoyl)phenyl]-S-methyl-N-[2-dimethylamino-ethyl]sulfoximide;

S-[4-(N-{2-[N-(5-chloro(2-pyridyl))carbamoyl]-4-chlorophenyl}carbamoyl)phenyl]-S-methyl-N-[(2-(2-hydroxyethyl)-methyl-amino)-ethyl]sulfoximide;

S-[4-(N-{2-[N-(5-chloro(2-pyridyl))carbamoyl]-4-chlorophenyl}carbamoyl)phenyl]-S-methyl-N-[2-(4-methylpiperazin-1-yl)-ethyl]sulfoximide;

S-[4-(N-{2-[N-(5-chloro(2-pyridyl))carbamoyl]-4-chlorophenyl}carbamoyl)phenyl]-S-methyl-N-[2-(4-morpholinyl)-ethyl]sulfoximide;

S-[4-(N-{2-[N-(5-chloro(2-pyridyl))carbamoyl]-4-chlorophenyl}carbamoyl)phenyl]-S-methyl-N-[2-(4-methyl-homopiperazinyl)-ethyl]sulfoximide;

(−)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide;

(+)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide;

S-[4-(N-{2-[N-(5-chloro(2-pyridyl))carbamoyl]-4-chlorophenyl}carbamoyl)phenyl]-S-methyl-N-(2-diethylamino-acetyl)sulfoximide hydrochloride;

S-[4-(N-{2-[N-(5-chloro(2-pyridyl))carbamoyl]-4-chlorophenyl}carbamoyl)phenyl]-S-(2-hydroxy ethyl)-sulfoximide;

S-(2-[4-(N-{2-[N-(5-chloro-2-pyridyl)carbamoyl]-4-chlorophenyl}carbamoyl)phenyl]-phenyl)-S-methyl sulfoximide;

S-(2-[4-(N-{2-[N-(5-chloro-2-pyridyl)carbamoyl]-4-chloro-6-methoxyphenyl}carbamoyl)phenyl]-phenyl)-S-methyl sulfoximide;

S-(2-[4-(N-{2-[N-(5-chloro-2-pyridyl)carbamoyl]-4-chlorophenyl}carbamoyl)phenyl]-phenyl)-S-methyl-N-acetyl sulfoximide;

S-(2-[4-(N-{2-[N-(5-chloro-2-pyridyl)carbamoyl]-4-chlorophenyl}carbamoyl)phenyl]-phenyl)-S-methyl-N-cyclopropylcarbonyl sulfoximide;

S-(2-[4-(N-{2-[N-(5-chloro-2-pyridyl)carbamoyl]-4-chlorophenyl}carbamoyl)phenyl]-phenyl)-S-methyl-N-methoxycarbonyl sulfoximide;

S-(2-[4-(N-{2-[N-(5-chloro-2-pyridyl)carbamoyl]-4-chlorophenyl}carbamoyl)phenyl]-phenyl)-S-methyl-N-methanesulfonyl sulfoximide;

S-(2-[4-(N-{2-[N-(5-chloro-2-pyridyl)carbamoyl]-4-chlorophenyl}carbamoyl)phenyl]-phenyl)-S-methyl-N-chloroacetyl sulfoximide;

S-(2-[4-(N-{2-[N-(5-chloro-2-pyridyl)carbamoyl]-4-chlorophenyl}carbamoyl)phenyl]-phenyl)-S-methyl-N-cyano sulfoximide;

S-(2-[4-(N-{2-[N-(5-chloro-2-pyridyl)carbamoyl]-4-chlorophenyl}carbamoyl)phenyl]-phenyl)-S-methyl-N-aminocarbonyl sulfoximide;
S-(2-[4-(N-{2-[N-(5-chloro-2-pyridyl)carbamoyl]-4-chlorophenyl}carbamoyl)phenyl]-phenyl)-S-methyl-N-(4-pyridylcarbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-(4-piperidinylcarbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-(1-ethyl-piperidine-4-carbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-cyanoacetyl sulfoximide;
S-(2-[4-(N-{2-[N-(5-chloro-2-pyridyl)carbamoyl]-4-chlorophenyl}carbamoyl)phenyl]-phenyl)-S-methyl-N-methoxyacetyl sulfoximide;
S-(2-[4-(N-{2-[N-(5-chloro-2-pyridyl)carbamoyl]-4-chlorophenyl}carbamoyl)phenyl]-phenyl)-S-methyl-N-(2-dimethylamino-acetyl)sulfoximide;
S-(2-[4-(N-{2-[N-(5-chloro-2-pyridyl)carbamoyl]-4-chlorophenyl}carbamoyl)phenyl]-phenyl)-S-methyl-N-(2-diethylamino-acetyl)sulfoximide;
S-(2-[4-(N-{2-[N-(5-chloro-2-pyridyl)carbamoyl]-4-chlorophenyl}carbamoyl)phenyl]-phenyl)-S-methyl-N-[2-(methyl-propyl-amino)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(carbamoylmethyl-methyl-amino)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[(2-pyrrolidin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[(2-piperidin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(4-aminopiperidinyl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(4-methylpiperazinyl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(piperazin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(imidazol-1-yl)-acetyl]sulfoximide.

The novel compounds of this invention may be prepared using the reactions and techniques described in this section. The various alternative routes represent processes for preparing compounds of the present invention and includes the preferred modes for preparing the compounds of the invention as known to the inventors. The reactions are performed in solvents appropriate to the reagents and materials employed and are suitable for the transformations being effected. It is understood by those skilled in the art that the nature and order of the synthetic steps presented may be varied for the purpose of optimizing the formation of one or more of the compounds of the present invention. It is also to be appreciated that the scheme as described may be suitably modified as required, so as to obtain specific compounds of the present invention. Such modifications/alterations should also be considered to be within the scope of the present invention as they are within the perview of a person skilled in the art.

Scheme 1: Synthesis of compounds of general formula (I) (When B represents a bond; other symbols are as defined earlier)

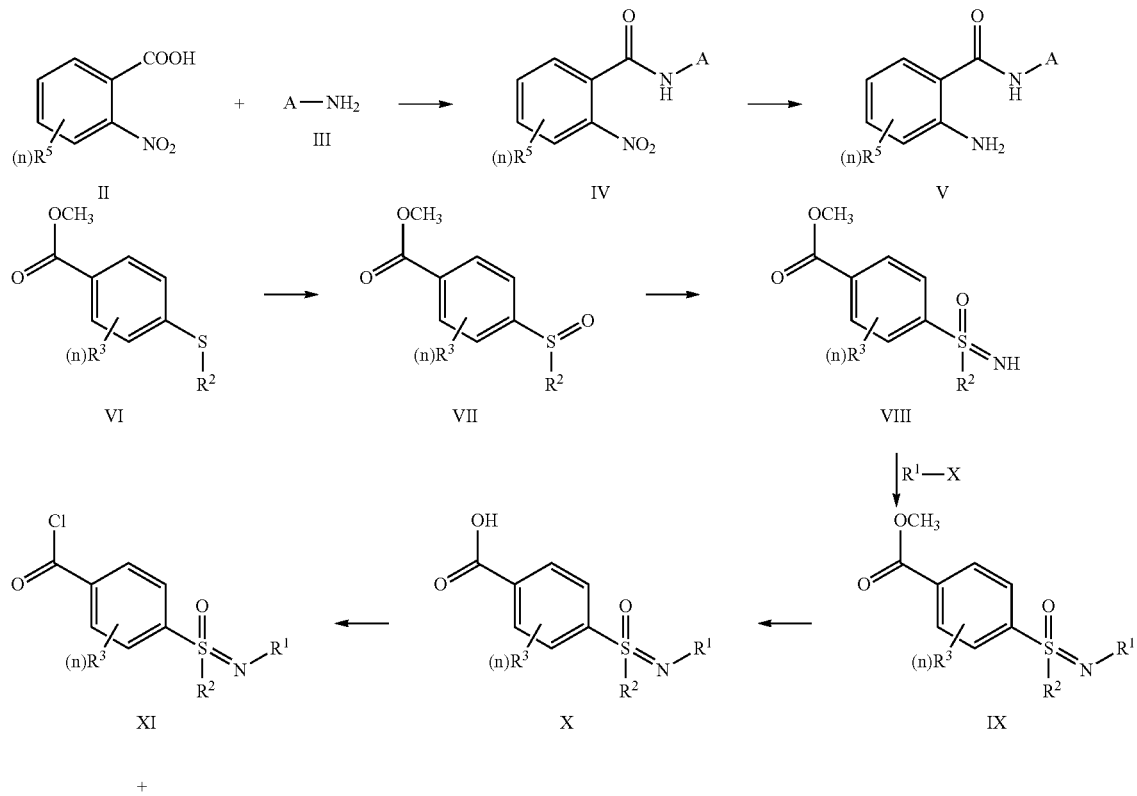

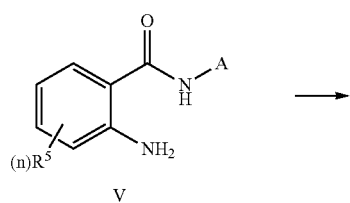 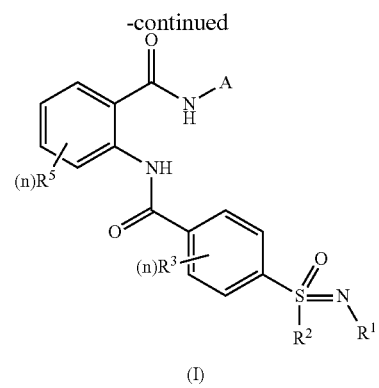

The compound (IV) can be obtained by coupling reaction of (II) and (III) using general amide bond formation techniques described in *Tetrahedron* 61 (2005) 10827-10852.

The compounds of general formula (V) can be obtained by reduction of (IV) using various techniques reported in literature. Most preferred techniques are reduction with $SnCl_2$, catalytic hydrogenation, Raney Ni/hydrazine hydrate etc.

The compounds of the general formula (VI) are either commercially available or prepared using general procedure given in *OSCV (II)* pg 580.

The compound (VII) can be obtained by oxidation of (VI) using various sulfur oxidation techniques known in the art. Most preferred techniques are oxidation with hydrogen peroxide, MCPBA and the like, in solvents like acetone, acetonitrile, dichloro methane (DCM) and the like or their suitable mixtures. Preferred temperature range is −50° C. to 30° C.

The compounds of the formula (VIII) can be obtained by treating (VII) with several amine donor groups reported in the literature. A preferred technique for preparation of (VIII) is using sodium azide-sulfuric acid reagents and chloroform as a solvent.

The compounds of formula (VIII) can be converted to compound (IX) using $R_1$—X, where X=any suitable leaving group for eg. Cl, Br, I etc. using suitable solvent and base. Preferred solvents are DCM, pyridine, toulene, THF and the like or their suitable mixtures. Preferred bases are triethyl amine (TEA), pyridine, diisopropyl ethylamine (DIPEA), sodium hydride and the like or their suitable mixtures.

Compound (IX) on hydrolysis with suitable metal hydroxides such be NaOH, KOH, LiOH etc gives compound (X).

Compound (X) may be converted to compound (XI) using various techniques known in art. Most preferred techniques are reaction with thionyl chloride or oxalyl chloride in solvents such as DCM, chloroform, toluene and the like or their suitable mixtures. Suitable temperature range may vary from 0-50° C.

Compound (XI) is then reacted with compound (V) to give (I) in solvents such as DCM, THF, acetonitrile and the like or their suitable mixtures using bases like TEA, diisopropyl ethylamine, pyridine and the like.

Scheme 2: Synthesis of compounds of general formula (I) (When B represents a bond; other symbols are as defined earlier)

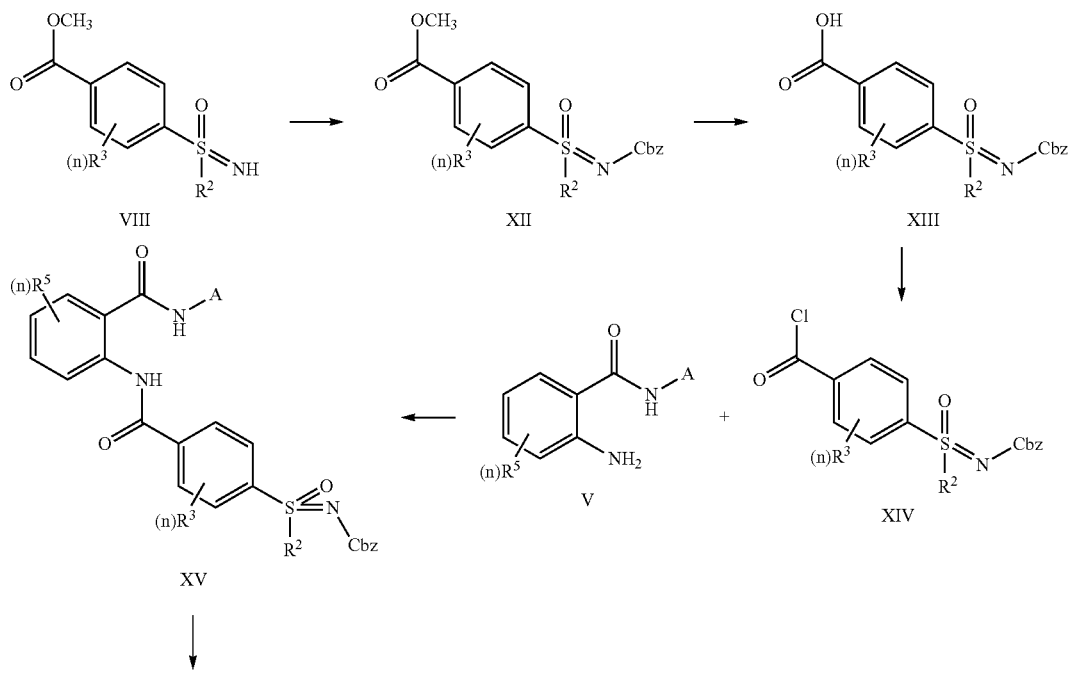

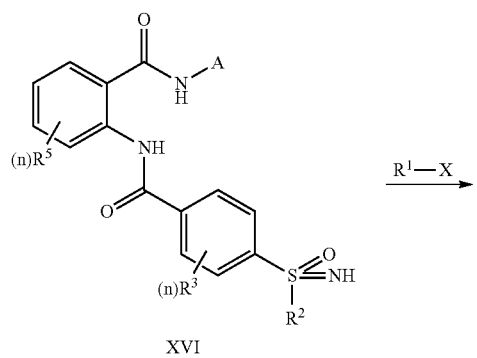

XVI

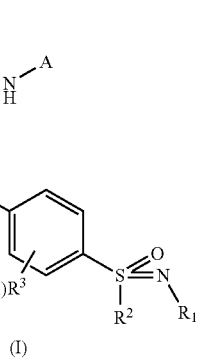

(I)

Alternatively, compound (VIII) is protected with suitable protecting groups such as carbamates, amides, sulfonamide, benzyl derivatives etc. to give compound (XII) using conditions similar as described earlier for the preparation of compound (IX). The compounds of the general formula (XIII) are prepared using conditions similar to those described for the preparation of (X) above.

The compounds of the general formula (XIV) are then prepared from (XIII) using conditions similar as described for the preparation of (XI).

Compound (XV) can be obtained by reaction of (XIV) with (V) using conditions similar to those described for the preparation of compound (I) above. The compound (XV) is then deprotected to give (XVI) using various deprotection techniques reported in literature. The compounds of the general formula (I) are then obtained by reaction of (XVI) with $R^1X$ using conditions similar to those described for the preparation of (IX).

Scheme 3: Synthesis of compounds of general formula (I) (When B does not represents a bond; other symbols are as defined earlier)

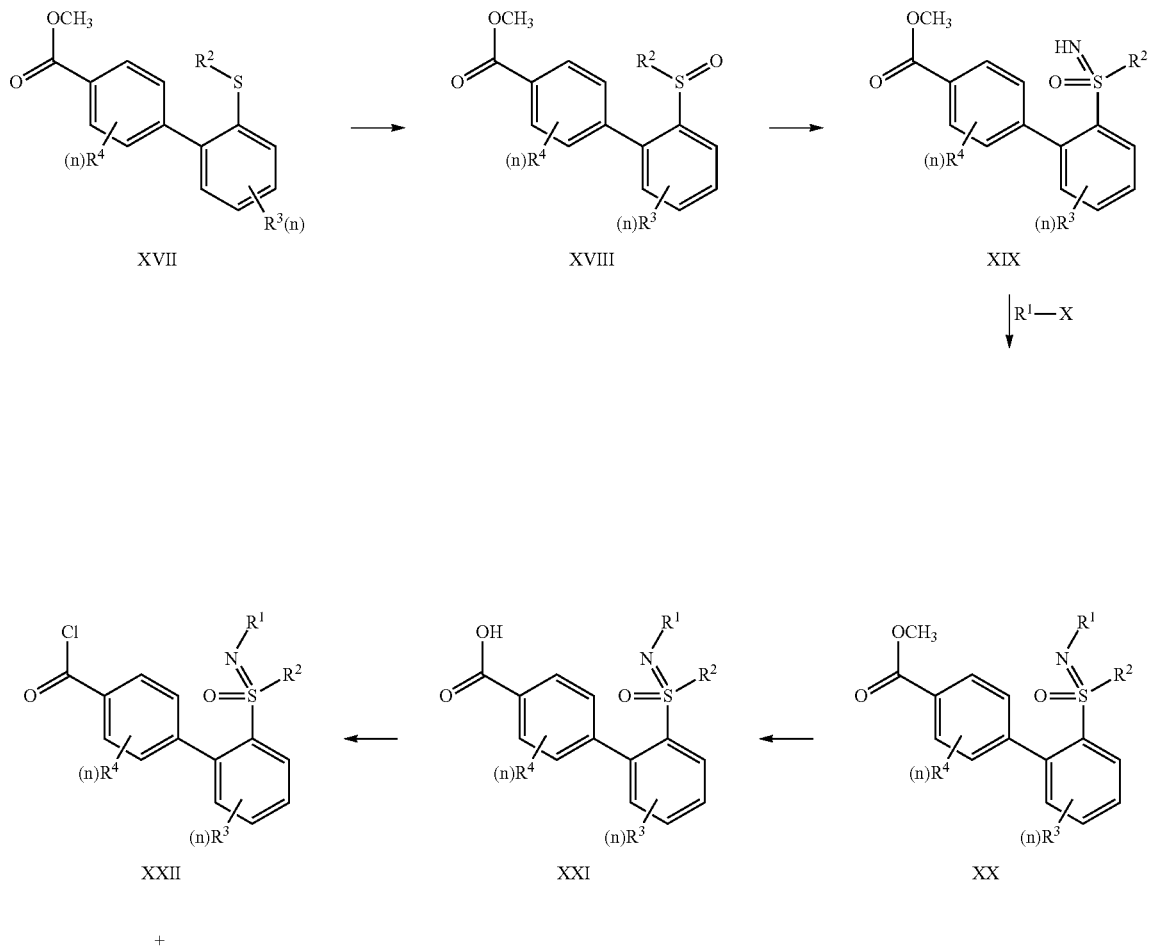

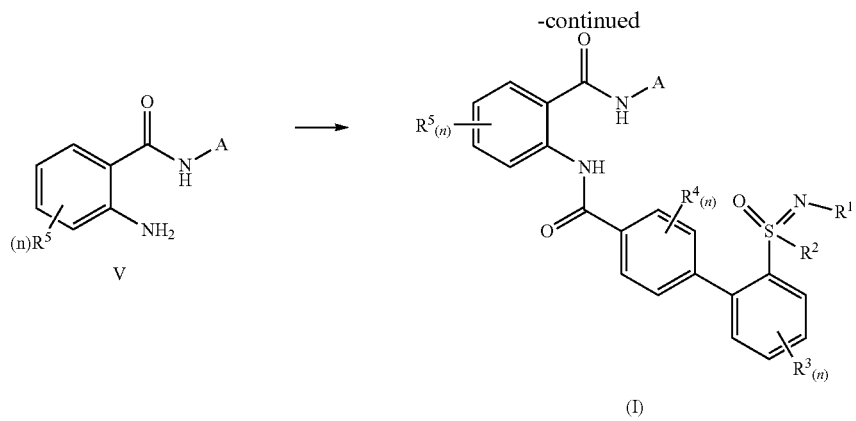

(I)

The compound (XVII) can be obtained by coupling reaction of appropriately substituted 4-iodomethyl benzoate and aryl boronic acids using general Suzuki coupling techniques.

The compound (XVIII) can be obtained by oxidation of (XVII) using conditions similar to those described for the preparation of (VII).

The compounds of the formula (XIX) can be obtained by treating (XVIII) with several amine donor groups reported in the literature. A preferred technique for preparation of (XIX) is sodium azide-sulfuric acid reagents and chloroform as a solvent The compounds of formula (XIX) can be converted to compound (XX) using $R_1$—X, where X=any suitable leaving group for eg. Cl, Br, I etc. using conditions similar to those described for the preparation of (IX).

Compound (XX) on hydrolysis with suitable metal hydroxides such be NaOH, KOH, LiOH and the like, gives compound (XXI).

Compound (XXI) can be converted to compound (XXII), using conditions similar to those described for the preparation of (XI) above.

Compound (XXII) is then reacted with compound (V) to give (I) in solvents like DCM, THF, acetonitrile and the like or their suitable mixtures; using bases such as TEA, diisopropyl ethylamine, pyridine and the like or their suitable mixtures.

Scheme 4: Synthesis of compounds of general formula (I) (When B represents a bond; other symbols are as defined earlier)

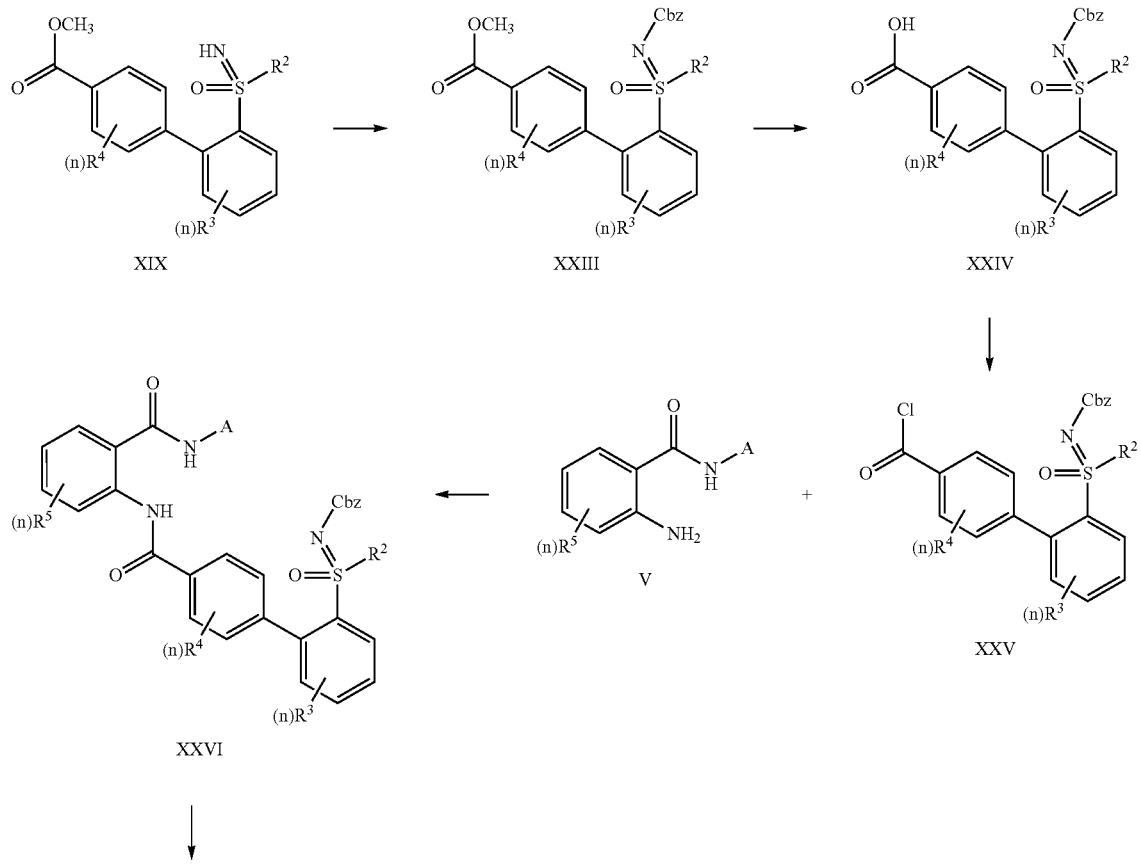

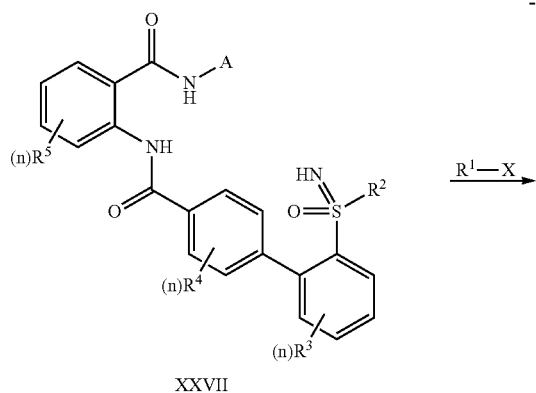

XXVII

R¹—X →

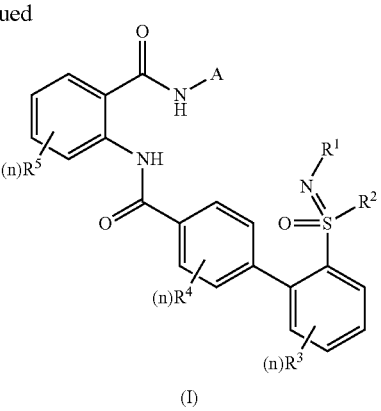

(I)

Alternatively, compound (XIX) is protected with suitable protecting groups such as carbamates, amides, sulfonamide, benzyl derivatives etc. to give compound (XXIII) using conditions similar as described earlier for the preparation of compound (IX). The compounds of the general formula (XXIV) are prepared using conditions similar to those described for the preparation of (X).

The compounds of the general formula (XXV) are then prepared from (XXIV) using conditions similar as described for the preparation of (XI).

Compound (XXVI) can be obtained by reaction of (XXV) with (V) using conditions similar to those described for the preparation of compound (I) above. The compound (XXVI) is then deprotected to give (XXVII) using various deprotection techniques reported in literature. The compounds of the general formula (I) are then obtained by reaction of (XXVII) with R¹—X, where X is as defined earlier, using conditions similar to those described for the preparation of (IX).

The invention is explained in greater detail by the examples given below, which are provided by way of illustration only and therefore should not be construed to limit the scope of the invention.

1H NMR spectral data given in the examples (vide infra) are recorded using a 400 MHz spectrometer (Bruker Topspin 2.0) and reported in δ scale. Tetramethyl silane is used as the internal standard.

EXAMPLE 1

Preparation of S-[4-(N-{2-[N-(5-chloro(2-pyridyl))carbamoyl]-4-chlorophenyl}carbamoyl)phenyl]-S-methyl Sulfoximide

Step 1: Preparation of 5-Chloro-N-(5-chloro-pyridin-2-yl)-2-nitro-benzamide

To a stirred solution of 5-chloro-2-nitro-benzoic acid (100 g, 0.4962 mol) in acetonitrile (500 mL) was added pyridine (121 mL, 1.48 mol) at 25-30° C. The reaction mixture was then cooled to 0-10° C. under nitrogen atmosphere. To this was added POCl₃ (54.6 mL, 0.5955 mol) drop wise by maintaining exothermicity. After stirring at 25-30° C. for 1 hr, reaction mixture was poured in cold water and filtered. Solid obtained was stirred in 500 mL of saturated solution of sodium bicarbonate for 10 min. Filtration and drying afforded 164 g of titled compound in 86% yield.

Step 2: Preparation of 2-Amino-5-chloro-N-(5-chloro-pyridin-2-yl)-benzamide

To a stirred solution of 5-Chloro-N-(5-chloro-pyridin-2-yl)-2-nitro-benzamide (26 g, 0.0833 mol) in ethyl acetate (170 mL) was added Stannous chloride dihydrate (75 g, 0.333 mol) at 25-30° C. After stirring at same temperature for 2 hr, reaction mixture was diluted with 250 mL ethyl acetate and made alkaline with aqueous ammonia solution. Reaction mixture was then filtered through hyflow bed and organic layer was dried over sodium sulfate. Evaporation of solvent afforded 19 g of titled compound in 81% yield.

Step 3: Preparation of 4-Methanesulfinyl-benzoic acid methyl ester

A mixture of 4-(Mercaptomethyl)-benzoic acid methyl ester (75.5 g, 0.414 mol) and V₂O₅ (754 mg, 0.0041 mol) in acetonitrile (755 mL) was cooled with stirring to −20 to −25° C. under nitrogen atmosphere. To this was added 50% hydrogen peroxide (15.5 g, 0.455 mol) drop wise in 20-30 min. The reaction mixture was stirred at 25-30° C. for 5 hr. Reaction mixture was diluted with 700 mL water and extracted with ethyl acetate. Evaporation and drying over sodium sulfate afforded 78.8 g of titled compound in 96% yield.

Step 4: Preparation of S-(4-Methoxycarbonyl)-phenyl-S-methyl sulfoximide

To a solution of 4-methanesulfinyl-benzoic acid methyl ester (78.5 g, 0.396 mol) in chloroform (780 mL) was added sodium azide (77.2 g, 1.188 mol) at 25° C. To this was added drop wise sulfuric acid (130 mL, 2.37 mol) at −20 to −25° C. under nitrogen atmosphere in 20-30 min. The reaction mixture was stirred at 25-30° C. for 12 hr and then at 45-50° C. for 3 hr. Chloroform was decanted from reaction mixture and remaining residue was made alkaline by using aqueous potassium carbonate solution. Ethyl acetate (1 L) was added to it and organic layer was separated out. Drying over sodium sulfate and evaporation afforded 63.6 g of titled compound in 75% yield.

Step 5: Preparation of S-(4-Methoxycarbonyl)-phenyl-S-methyl-N-Benzyloxy carbonyl Sulfoximide To a stirring solution of S-(4-Methoxycarbonyl)-phenyl-S-methyl sulfoximide (26 g, 0.122 mol) in dichloromethane (260 mL) was added pyridine (10.6 g, 0.134 mol). To this was added benzyloxy carbonyl chloride (22.9 g, 0.134 mol) at 15-20° C. under nitrogen atmosphere. The reaction mixture was stirred at 25-30° C. for 3 hr and then diluted with dichloromethane (300 mL). Organic layer was washed with water (600 mL) and evaporated after drying over sodium sulfate to get 39.5 g of titled compound in 94% yield.

Step 6: Preparation of S-(4-Carboxy)-phenyl-S-methyl-N-benzyloxycarbonyl sulfoximide To a stirring solution of sodium hydroxide (6.74 g, 0.168 mol) in the solvent mixture of water (195 mL) and THF (195 mL) was added product of step 5 (39 g, 0.112 mol). Reaction mixture was stirred at 25-30° C. for 3 hr and then diluted with water (300 ml). Aqueous layer was washed with MTBE. Aqueous layer was then cooled to 0° C. and acidified with diluted HCl. Extracted with ethyl acetate (1.4 L) which on drying over sodium sulfate and evaporation afforded 33 g of titled compound in 88% yield.

Step 7: Preparation of S-[4-(N-{2-[N-(5-chloro(2-pyridyl))carbamoyl]-4-chloro phenyl}carbamoyl)phenyl]-S-methyl-N-benzyloxycarbonyl Sulfoximide To a stirring solution of S-(4-Carboxy)-phenyl-S-methyl-N-benzyloxycarbonyl sulfoximide (89 g, 0.267 mol) and DMF (0.89 mL) in DCM (890 mL) was added oxalyl chloride (40.73 g, 0.327 mol) at 10-15° C. under nitrogen atmosphere. Reaction mixture was stirred at 25-30° C. for 3 hr and then evaporated to dryness. Acid chloride obtained was dissolved in dry THF (350 mL) and was added to a solution containing 2-amino-5-chloro-N-(5-chloro-pyridin-2-yl)-benzamide (67.7 g, 0.240 mol) in THF (273 mL) at 10-15° C. After stirring at 25-30° C. for 12 hr, reaction mixture was quenched with water (150 mL). Product was extracted with chloroform (1 L) which on drying over sodium sulfate, evaporation and crystallization in ethyl acetate afforded 102 g of titled compound in 64% yield.

Step 8: Preparation of S-[4-(N-{2-[N-(5-chloro(2-pyridyl))carbamoyl]-4-chloro phenyl}carbamoyl)phenyl]-S-methyl sulfoximide Sulfuric acid (50 mL) was cooled to 0-5° C. To this was added product of step 7 (10 g, 0.016 mol) and reaction mixture was stirred at same temperature for 15-20 min. Above reaction mixture was slowly poured in chilled water and basified using aqueous potassium carbonate solution. Precipitated product was filtered and washed with water. Drying afforded 7 g of titled compound in 90% yield.

$^1$H NMR:(DMSO-d6, 400 MHz)δ: 11.25(1H, s),11.18(1H, s),8.43 (1H,d),8.12(2H, t), 8.06(4H,s),7.93(2H,m),7.65(1H, dd),4.38(1H,s),3.10(3H,s).

EXAMPLE 2

Preparation of S-[4-(N-{2-[N-(5-chloro(2-pyridyl))carbamoyl]-4-methoxyphenyl}carbamoyl)phenyl]-S-methyl Sulfoximide Prepared using similar procedure as that of example 1 but using 5-methoxy-2-nitrobenzoic acid in step 1 instead of 5-chloro-2-nitrobenzoic acid.

$^1$H NMR (DMSO-d6, 400 MHz)δ: 11.11(1H,s),10.09(1H, s),8.42(1H,d),8.11(1H,d), 8.04(4H,m),7.40(2H,m),7.19(1H, d),7.16(1H,d),4.3(1H,s),3.84(3H,s),3.10(3H,s). Yield-61%

EXAMPLE 3

Preparation of S-[4-(N-{2-[N-(5-chloro(2-pyridyl))carbamoyl]-4-chlorophenyl}carbamoyl)phenyl]-S-ethyl Sulfoximide Prepared using similar procedure as that of example 1 but using 4-(Mercaptoethyl)-benzoic acid methyl ester in step 3 instead of 4-(Mercaptomethyl)-benzoic acid methyl ester.

$^1$H NMR(DMSO-d6,400 MHz)δ: 11.25(1H,s),11.17(1H, s),8.43(1H,d),8.42(2H,dd), 8.09(2H,m), 8.01(2H,m), 7.95 (1H,m),7.93(1H,m),7.66(1H,dd),4.37(1H,s),3.18(2H,q), 1.07(3H,t). Yield=67%

EXAMPLE 4

Preparation of S-(2-[4-(N-{2-[N-(5-chloro-2-pyridyl)carbamoyl]-4-chlorophenyl}carbamoyl)phenyl]-phenyl)-S-methyl sulfoximide

Step 1: Preparation of 2'-Methylsulfanyl-biphenyl-4-carboxylic acid methyl ester To a stirring solution of 4-iodobenzoic acid methyl ester (5 g, 0.0019 mol), sodium carbonate (4.04 g, 0.038 mol) and Palladium acetate (4.2 mg, 0.00019 mol) in methanol (30 mL), was added 2-methylmercapto phenyl boronic acid (3.53 g, 0.02 mol) in one lot at 25-30° C. After reflux of 30 min., reaction mixture was poured in ice cold water (100 mL) and product was extracted in ethyl acetate (250 mL). Column purification (100-200 mesh silica gel, 5% hexane in ethyl acetate) gave 4 g of titled product in 81% yield.

Step 2: Preparation of 2'-Methanesulfinyl-biphenyl-4-carboxylic acid methyl ester Prepared using similar procedure as that of Example 1, step 3 in 95% yield.

Step 3: Preparation of S-(2-(4-methoxycarbonyl)-phenyl)-phenyl-S-methyl sulfoximide Prepared using similar procedure as that of Example 1, step 4 in 84% yield.

$^1$H NMR(DMSO-d6,400 MHz)δ: 8.16(1H,d),7.9(2H, d),7.6 (2H,t),7.5(2H,d),7.32(1H, d), 4.2(1H,s), 3.8(3H,s),2.7 (3H,s).

Step 4: Preparation of S-(2-(methoxycarbonyl)-phenyl)-phenyl-S-methyl-N-benzyl oxycarbonyl sulfoximide Prepared using similar procedure as that of Example 1, step 5 in 93% yield.

Step 5: Preparation of S-(2-(carboxy)-phenyl)-phenyl-S-methyl-N-benzyl oxycarbonyl sulfoximide Prepared using similar procedure as that of Example 1, step 6 in 80% yield.

Step 6: Preparation of S-(2-[4-(N-{2-[N-(5-chloro-2-pyridyl)carbamoyl]-4-chloro phenyl}carbamoyl)phenyl]-phenyl)-S-methyl-N-benzyloxycarbonyl sulfoximide Prepared using similar procedure as that of Example 1, step 7 in 88% yield.
Product obtained was column purified using 100-200 mesh size silica gel and 40% hexane in ethyl acetate.

Step 7: Preparation of Preparation of S-(2-[4-(N-{2-[N-(5-chloro-2-pyridyl) carbamoyl]-4-chlorophenyl}carbamoyl)phenyl]-phenyl)-S-methyl sulfoximide Prepared using similar procedure as that of Example 1, step 8 in 88% yield.
$^1$H NMR(DMSO-d6,400 MHz)δ:11.2(2H,d),8.4(1H,s), 8.2(1H,d),8.1(2H,m),7.9(4H,m), 7.6(3H,m),7.3(2H,m),7.3(1H,m),4.3(1H,s),2.7(3H,s).

EXAMPLE 5

Preparation of S-(2-[4-(N-{2-[N-(5-chloro-2-pyridyl)carbamoyl]-4-chloro-6-methoxy phenyl}carbamoyl)phenyl]-phenyl)-S-methyl Sulfoximide Step 1: Preparation of N-(5-Chloro-pyridin-2-yl)-3-methoxy-2-nitro-benzamide Prepared using similar procedure as that of Example 1, step 1 using appropriate starting materials. Yield: 96%

Step 2: Preparation of 2-Amino-N-(5-chloro-pyridin-2-yl)-3-methoxy-benzamide

Prepared using similar procedure as that of Example 1, step 2 using appropriate starting materials. Yield: 42%

Step 3: Preparation of S-(2-[4-(N-{2-[N-(5-chloro-2-pyridyl)carbamoyl]-4-chloro-6-methoxyphenyl}carbamoyl)phenyl]-phenyl)-S-methyl-N-benzyloxycarbonyl sulfoximide Prepared using similar procedure as that of Example 1, step 7 using appropriate starting materials. Yield: 16%

Step 4: Preparation of S-(2-[4-(N-{2-[N-(5-chloro-2-pyridyl)carbamoyl]-4-chloro-6-methoxyphenyl}carbamoyl)phenyl]-phenyl)-S-methyl sulfoximide Prepared using similar procedure as that of Example 1, step 8 in 96% yield.
$^1$H NMR(DMSO-d6,400 MHz)δ: 10.83 (1H,s),9.82(1H, s),8.36(1H,d), 8.15(1H,m), 8.13(1H,d),8.07(1H,m),7.89(3H,m),7.6(2H,m),7.65(2H,m),7.37(1H,d),7.28 (1H,d), 4.3(1H,S),3.86(3H,s),2.74(3H,s).

EXAMPLE 6

Preparation of S-[4-(N-{2-[N-(5-chloro(2-pyridyl))carbamoyl]-4-chlorophenyl}carbamoyl)phenyl]-S-methyl-N-chloroacetyl Sulfoximide To a stirring solution of S-[4-(N-{2-[N-(5-chloro(2-pyridyl))carbamoyl]-4-chlorophenyl}carbamoyl)phenyl]-S-methyl sulfoximide (0.5 g, 0.001 mol) and pyridine (2 mL) in DCM (20 mL) was added Chloroacetyl chloride (244 mg, 0.00215 mol) at 0° C. After few minutes, reaction mixture was diluted with water (10 ml). Organic layer was separated, dried and distilled out to get 300 mg of desired product in 52% yield.
$^1$H NMR(DMSO-d6,400 MHz)δ: 11.25(1H,s),11.18(1H, s),8.43(1H,d),8.09(6H,m), 7.96(1H,d),7.89(1H,d),7.66(1H, d),4.26(2H,s),3.56(3H,s).

Using appropriate starting materials and suitable modifications of the process described in example 6, including suitable addition and/or deletion of steps as may be necessary, well within the scope of a person skilled in the art, the following compounds were prepared in an analogous manner.

EXAMPLE 7

S-(2-[4-(N-{2-[N-(5-chloro-2-pyridyl)carbamoyl]-4-chlorophenyl}carbamoyl)phenyl]-phenyl)-S-methyl-N-chloroacetyl sulfoximide $^1$H NMR(DMSO-d6,400 MHz)δ: 11.29(1H,s),11.23(1H, s),8.44(1H,d),8.43(1H,dd), 8.1(2H,m),7.9(4H,m),7.81(2H, m),7.67(1H,dd),7.66(2H,dd),7.4(1H,dd),4.05(1H, d), 3.91 (1H,d),3.25(3H,s); Yield: 96%

EXAMPLE 8

S-[4-(N-{2-[N-(5-chloro(2-pyridyl))carbamoyl]-4-chlorophenyl}carbamoyl)phenyl]-S-methyl-N-acetyl sulfoximide $^1$H NMR (DMSO-d$_6$, 400 MHz)δ: 11.25 (1H,s), 11.18 (1H,s), 8.43(1H,s), 8.08 (6H,m), 7.92 (2H,m), 7.66 (1H,dd), 3.45(3H,s), 1.97(3H,s); Yield=61%

EXAMPLE 9

S-(2-[4-(N-{2-[N-(5-chloro-2-pyridyl)carbamoyl]-4-chloro phenyl}carbamoyl)phenyl]-phenyl)-S-methyl-N-acetyl sulfoximide $^1$HNMR(DMSO-d6,400 MHz)δ: 11.26(1H,s),11.22(1H, s),8.43(1H,d), 8.24(1H,d), 8.12(2H,dd),7.95(4H,m),7.77 (2H,m),7.68(1H,dd),7.5(2H,d),7.3(1H,d),3.18(3H,s), 1.7(3H,s); Yield: 67%

EXAMPLE 10

S-[4-(N-{2-[N-(5-chloro(2-pyridyl))carbamoyl]-4-chlorophenyl}carbamoyl)phenyl]-S-methyl-N-propionyl Sulfoximide $^1$H NMR(DMSO-d6,400 MHz)δ: 11.25(1H,s),11.17(1H, s),8.43(1H,d), 8.08(6H,m),7.93(2H,m),7.67(1H,q),3.45(3H, s),2.27(2H,q),0.95(3H,t); Yield=46%

EXAMPLE 11

S-[4-(N-{2-[N-(5-chloro(2-pyridyl))carbamoyl]-4-chlorophenyl}carbamoyl)phenyl]-S-methyl-N-methoxycarbonyl sulfoximide $^1$H NMR(DMSO-d$_6$,400 MHz)δ: 11.25(1H,s),11.17(1H, s),8.43(1H,s), 8.08 (6H,m) 7.92(2H,m),7.66 (1H,d),3.51(3H, s),3.47(3H,s); Yield=57%

EXAMPLE 12

S-(2-[4-(N-{2-[N-(5-chloro-2-pyridyl)carbamoyl]-4-chlorophenyl}carbamoyl)phenyl]-phenyl)-S-methyl-N-methoxycarbonyl sulfoximine $^1$H NMR(DMSO-d6,400 MHz)δ: 11.2(2H,bd),8.4(1H,s), 8.0(2H,d),7.9(4H,m), 7.83(4H,m),7.78(2H,m),7.3(1H,d),3.5 (3H,s),2.98(3H,s); Yield: 72%

EXAMPLE 13

S-[4-(N-{2-[N-(5-chloro(2-pyridyl))carbamoyl]-4-chlorophenyl}carbamoyl)phenyl]-S-methyl-N-methanesulfonyl sulfoximine $^1$H NMR(DMSO-d6,400 MHz)δ: 11.26(1H,s),11.19(1H, s),8.43(1H,d),8.10(4H,m), 8.06(2H,m),7.94(2H,m),7.73 (1H,t),3.64(3H,s),3.02(3H,s); Yield-51%

EXAMPLE 14

S-(2-[4-(N-{2-[N-(5-chloro-2-pyridyl)carbamoyl]-4-chlorophenyl}carbamoyl)phenyl]-phenyl)-S-methyl-N-methanesulfonyl sulfoximine $^1$H NMR (DMSO-d$_6$, 400 MHz)δ: 11.2(2H,d), 8.8(1H,d), 8.4(1H,s), 8.2(2H,m), 8.0(1H,d), 7.9(4H,m),7.83(3H,m), 7.68(1H,m),7.60(1H,d),7.4(1H,m)2.68(3H,s); Yield: 43%

EXAMPLE 15

Preparation of S-[4-(N-{2-[N-(5-chloro(2-pyridyl)) carbamoyl]-4-chlorophenyl}carbamoyl)phenyl]-S-methyl-N-cyano sulfoximine To a stirring solution of S-[4-(N-{2-[N-(5-chloro(2-pyridyl))carbamoyl]-4-chlorophenyl}carbamoyl)phenyl]-S-methyl sulfoximine (50 mg, 0.000108 mol) and DMAP (14.5 mg, 0.000216 mol) in DCM (1 mL) was added cyanogen bromide (23 mg, 0.000216 mol) at 25° C. Reaction mixture was stirred at 25-30° C. for 18 hr and then diluted with DCM (10 mL). Organic layer was washed with dil.HCl. Drying over sodium sulfate and evaporation afforded 20 mg of titled compound in 37% yield.

$^1$H NMR (DMSO-d6, 400 MHz)δ: 11.25(1H,s), 11.19(1H, s), 8.42(1H,s), 8.30(4H,m), 8.12(1H,d), 8.06(1H,d),8.04(2H, m),7.88(1H,m)3.78(3H,s).

EXAMPLE 16

S-(2-[4-(N-{2-[N-(5-chloro-2-pyridyl)carbamoyl]-4-chlorophenyl}carbamoyl)phenyl]-phenyl)-S-methyl-N-cyano sulfoximine Prepared using similar procedure as that of Example 15.
$^1$H NMR(DMSO-d6,400 MHz)δ: 11.26(1H,s),11.20(1H, s),8.44(1H,s),8.43(2H,d), 8.21(1H,m),8.13(5H,m),7.98(1H, m),7.92(1H,m),7.86(2H,m),7.51(1H,s),3.4(3H,s).
Yield: 40%

EXAMPLE 17

S-[4-(N-{2-[N-(5-chloro(2-pyridyl))carbamoyl]-4-chlorophenyl}carbamoyl)phenyl]-S-methyl-N-carbamoyl sulfoximine Sulfuric acid (0.5 mL) was cooled to 5-10° C. To this was added product of Example 15 (150 mg, 0.38 mmol) and reaction mixture was stirred at 25-30° C. for 3 hr. Above reaction mixture was slowly poured in chilled water. Precipitated product was filtered and washed with water. Drying afforded 70 mg of titled compound in 45% yield.

$^1$H NMR(DMSO-d6,400 MHz)δ: 11.26(1H,s),11.19(1H, s),8.43(1H,d), 8.11(1H,m), 8.04(3H,m),7.92(2H,m),7.68 (2H,m),7.68(1H,m)6.45(1H,bs),6.05(1H,bs),3.37(3H,s).

EXAMPLE 18

S-(2-[4-(N-{2-[N-(5-chloro-2-pyridyl)carbamoyl]-4-chlorophenyl}carbamoyl)phenyl]-phenyl)-S-methyl-N-aminocarbonyl sulfoximine Prepared using similar procedure as that of Example 17 in 43% yield.
$^1$H NMR (DMSO-d$_6$, 400 MHz)δ: 11.29(1H,s), 11.22(1H, s), 8.44(1H,d), 8.24(1H,d), 8.0(2H, m), 7.9(5H,m), 7.7(4H, m), 7.69 (2H,d), 7.3 (1H,d), 2.9 (3H, s).

EXAMPLE 19

Preparation of S-[4-(N-{2-[N-(5-chloro(2-pyridyl)) carbamoyl]-4-chlorophenyl}carbamoyl)phenyl]-S-methyl-N-(tert-butoxycarbonylamino-acetyl)sulfoximine To a stirring solution of S-[4-(N-{2-[N-(5-chloro(2-pyridyl))carbamoyl]-4-chlorophenyl}carbamoyl)phenyl]-S-methyl sulfoximine (50 mg, 0.1082 mmol) and Boc protected Glycine (19 mg, 0.1082 mmol) in DMF (2 mL), was added EDCI (31 mg, 0.162 mmol) followed by catalytic amount of DMAP. The reaction mixture was stirred at 25-30° C. for 4 hr and then diluted with water (10 mL). Product obtained was extracted with chloroform (25 mL). Chloroform layer after drying over sodium sulfate and evaporation gave 25 mg of titled compound in 37% yield.

$^1$H NMR(DMSO-d6,400 MHz)δ: 11.26(2H,bs),8.42(1H, bs),8.10(5H,bs),7.91(2H,bs), 7.64(1H,bs),6.91(1H,bs),3.71 (2H,s),3.61(3H,s),1.33(9H,s).

Using appropriate starting materials and suitable modifications of the process described in Example 19, including suitable addition and/or deletion of steps as may be necessary, well within the scope of a person skilled in the art, the following compounds were prepared in an analogous manner.

EXAMPLE 20

S-[4-(N-{2-[N-(5-chloro(2-pyridyl))carbamoyl]-4-chlorophenyl}carbamoyl)phenyl]-S-methyl-N-cyclopropylcarbonyl sulfoximine $^1$H NMR (DMSO-d$_6$, 400 MHz)δ: 11.25(1H,s), 11.16(1H, s), 8.43(1H,d), 8.08(6H,m), 7.94(2H,m), 7.68(1H,dd), 3.50 (3H,s), 1.61(1H,m), 0.73(4H,t); Yield=13%

EXAMPLE 21

S-(2-[4-(N-{2-[N-(5-chloro-2-pyridyl)carbamoyl]-4-chlorophenyl}carbamoyl)phenyl]-phenyl)-S-methyl-N-cyclopropylcarbonyl sulfoximine $^1$H NMR(DMSO-d$_6$,400 MHz)δ: 11.3 (2H,bs),8.42(1H, d),8.38(1H,m),8.10(2H,m), 7.95(4H,m),7.77(2H,m),7.62 (1H,d), 7.38(2H,dd),7.36(1H,d),3.31(3H,s), 1.32(1H,m), 0.66(3H,m),0.61(1H,m); Yield: 77%

EXAMPLE 22

S-[4-(N-{2-[N-(5-chloro(2-pyridyl))carbamoyl]-4-chlorophenyl}carbamoyl)phenyl]-S-methyl-N-aminocarbonylcarbonyl sulfoximide $^1$H NMR (DMSO-d$_6$, 400 MHz)δ: 11.26 (1H,s), 11.18 (1H,s), 8.42 (1H,d), 8.10(6H,m), 7.92(2H,m), 7.82(1H,m), 7.68(1H,m),7.57(1H,d),3.62(3H,s); Yield=11%

EXAMPLE 23

S-[4-(N-{2-[N-(5-chloro(2-pyridyl))carbamoyl]-4-chlorophenyl}carbamoyl)phenyl]-S-methyl-N-(4-pyridylcarbonyl)sulfoximide $^1$H NMR (DMSO-d6, 400 MHz)δ: 11.25(1H,s),11.19(1H,s),8.73(2H,d),8.41(1H,d), 8.14(2H,d),8.07(4H,m),7.92(2H,m),7.86(2H,t),7.66(1H,dd),3.71(3H,s); Yield=73%

EXAMPLE 24

S-(2-[4-(N-{2-[N-(5-chloro-2-pyridyl)carbamoyl]-4-chlorophenyl}carbamoyl)phenyl]-phenyl)-S-methyl-N-(4-pyridylcarbonyl)sulfoximide $^1$H NMR (DMSO-d$_6$, 400 MHz)δ:11.28(1H,s),11.14(1H,s),8.6(2H,d), 8.44(1H,d), 8.25 (2H,m),8.12(1H,dd),7.95(3H,m),7.88(4H,m),7.66(1H,d),7.47(2H,dd),7.40(2H,d),3.44 (3H,s); Yield: 75%

EXAMPLE 25

S-[4-(N-{2-[N-(5-chloro(2-pyridyl))carbamoyl]-4-chlorophenyl}carbamoyl)phenyl]-S-methyl-N-(4-piperidinylcarbonyl)sulfoximide Prepared using Boc protected piperidine-4-carboxylic acid. Product obtained was deprotected with TFA to give titled compound in 78% yield.
$^1$H NMR (DMSO-d$_6$, 400 MHz)δ: 8.40(1H,d), 8.13(4H,m), 8.03(2H,m), 7.91(2H,dd), 7.61(1H,dd), 3.46(3H,s), 3.13 (2H,bd), 2.85(2H,bt), 1.93(2H,bd), 1.61(2H,bt).

EXAMPLE 26

S-(2-[4-(N-{2-[N-(5-chloro-2-pyridyl)carbamoyl]-4-chlorophenyl}carbamoyl)phenyl]-phenyl)-S-methyl-N-(4-piperidinylcarbonyl)sulfoximide Prepared using Boc protected piperidine-4-carboxylic acid. Product obtained was deprotected with TFA to give titled compound in 78% yield.
$^1$H NMR (DMSO-d6, 400 MHz)δ: 8.53 (1H,d), 8.39(1H,s), 8.22(4H,m),8.11(1H,s) 7.8(3H,m),7.5(4H,m),2.74(4H,t), 2.64(3H,s),2.36 (1H,m),1.79(4H,m).

EXAMPLE 27

S-[4-(N-{2-[N-(5-chloro(2-pyridyl))carbamoyl]-4-chlorophenyl}carbamoyl)phenyl]-S-methyl-N-(1-Ethyl-piperidine-4-carbonyl)sulfoximide Product of Example 25 was ethylated using standard N-alkylating procedure with ethyl iodide to give titled compound in 71% yield.
$^1$H NMR (DMSO-d$_6$, 400 MHz)δ: 8.42(1H,d), 8.14(4H,bd), 8.08(2H,m), 7.92(2H,bs), 7.61(1H,bs),3.46(3H,s),2.82 (2H,bs),2.31(2H,bs),2.16(1H,bs),1.97(1H,bs),1.77(2H,bs), 1.22 (2H,bt),0.96(3H,t).

EXAMPLE 28

S-(2-[4-(N-{2-[N-(5-chloro-2-pyridyl)carbamoyl]-4-chlorophenyl}carbamoyl)phenyl]-phenyl)-S-methyl-N-(1-ethyl-piperidine-4-carbonyl)sulfoximide Product of Example 26 was ethylated using standard N-alkylating procedure with ethyl iodide to give titled compound in 77% yield.
$^1$H NMR (DMSO-d$_6$, 400 MHz)δ: 11.22(2H,bs), 8.47(1H,d),8.44(1H,d),8.28(2H,m), 8.12 (4H,m),7.79(2H,m),7.72 (1H,d),7.38(2H,d),7.37(1H,d),3.21 (3H, s),2.87(2H,m),2.20 (2H,m),1.71(3H,m),1.65(2H,m),1.39(2H,t),0.84(3H,t).

EXAMPLE 29

S-[4-(N-{2-[N-(5-chloro(2-pyridyl))carbamoyl]-4-chlorophenyl}carbamoyl)phenyl]-S-methyl-N-(1-acetyl-piperidine-4-carbonyl)sulfoximide Product of Example 25 was acetylated using standard N-acetylating procedure with acetyl chloride to give titled compound in 87% yield.
$^1$H NMR (DMSO-d6, 400 MHz)δ: 11.24(1H,s), 11.17(1H,s), 8.4(1H,d,), 8.1(6H,m), 7.9(2H,m), 7.6(1H,d), 3.34(4H,m), 2.64(3H,s), 2.36(1H,m), 2.02(3H,s), 1.79(4H,m).

EXAMPLE 30

S-[4-(N-{2-[N-(5-chloro(2-pyridyl))carbamoyl]-4-chlorophenyl}carbamoyl)phenyl]-S-methyl-N-cyanoacetyl sulfoximide $^1$H NMR (DMSO-d6, 400 MHz)δ: 11.25(1H,s),11.19(1H,s),8.43(1H,d),8.1(6H,m), 7.9(2H,d,d),7.6(1H,d)3.8(2H,s)3.5 (3H,s); Yield=25%

EXAMPLE 31

S-(2-[4-(N-{2-[N-(5-chloro-2-pyridyl)carbamoyl]-4-chlorophenyl}carbamoyl)phenyl]-phenyl)-S-methyl-N-cyanoacetyl sulfoximide $^1$H NMR (DMSO-d6, 400 MHz)δ: 11.27(1H,s), 11.24(1H,s), 8.44(1H,d), 8.26(1H,d), 8.12(2H,m), 7.94(4H,m),7.8(2H,m),7.6(1H,d),7.54(2H,d),7.4(1H,d),3.66(1Hd), 3.46(1H,d), 3.26(3H,s); Yield: 30%

EXAMPLE 32

S-[4-(N-{2-[N-(5-chloro(2-pyridyl))carbamoyl]-4-chlorophenyl}carbamoyl)phenyl]-S-methyl-N-methoxyacetyl sulfoximide $^1$H NMR (DMSO-d6, 400 MHz)δ: 11.25(1H,s), 11.18(1H,s), 8.57(1H,d),8.42(1H,s), 7.92 (4H,m),7.77(2H,m),7.66(1H,dd),7.37(1H,q),3.93(2H,s),3.51(3H,s),3.25(3H,s); Yield=69%

EXAMPLE 33

S-[4-(N-{2-[N-(5-chloro(2-pyridyl))carbamoyl]-4-methoxyphenyl}carbamoyl)phenyl]-S-methyl-N-methoxyacetyl sulfoximide $^1$H NMR (DMSO-d6, 400 MHz)δ: 11.15(1H,s), 10.097 (1H,s), 8.42(1H,d), 8.07(5H,m), 7.92(2H,m),7.18(1H,d), 7.160(1H,d),4.014(2H,s),3.847(3H,s),3.515(3H,s),3.17 (3H); Yield=77%

EXAMPLE 34

S-[4-(N-{2-[N-(5-chloro(2-pyridyl))carbamoyl]-4-chlorophenyl}carbamoyl)phenyl]-S-ethyl-N-methoxyacetyl sulfoximide $^1$H NMR (DMSO-d6, 400 MHz)δ: 11.24(1H,s), 11.17(1H, s), 8.42(1H,d), 8.12(4H,m), 8.03(2H,m), 7.95(2H,m), 7.89 (1H,d),3.96(2H,q),3.63(2H,m),3.25(3H,s),1.09(3H,t). Yield: 65%

EXAMPLE 35

S-(2-[4-(N-{2-[N-(5-chloro-2-pyridyl)carbamoyl]-4-chlorophenyl}carbamoyl)phenyl]-phenyl)-S-methyl-N-methoxyacetyl sulfoximide $^1$H NMR (DMSO-d$_6$, 400 MHz)δ: 11.26(2H,d), 8.44(1H, d),8.23(1H,d),8.12(2H,m), 7.94(4H,m),7.8(3H,m),7.5(2H, d),7.4(1H,d),3.59(2H,m),3.23(3H,s),3.18(3H,s); Yield: 47%

EXAMPLE 36

S-[4-(N-{2-[N-(5-chloro(2-pyridyl))carbamoyl]-4-chlorophenyl}carbamoyl)phenyl]-S-methyl-N-ethoxyacetyl sulfoximide $^1$H NMR (DMSO-d6, 400 MHz)δ: 11.25(1H,s), 11.18(1H, s), 8.43(1H,d),8.08(6H,m), 7.92(2H,m),7.68(1H,q),3.92(2H, s),3.51(3H,s),3.42(2H,q),1.18(3H,t); Yield: 58%

EXAMPLE 37

S-[4-(N-{2-[N-(5-chloro(2-pyridyl))carbamoyl]-4-chlorophenyl}carbamoyl)phenyl]-S-methyl-N-(acetylamino-acetyl)sulfoximide $^1$H NMR (DMSO-d$_6$, 400 MHz)δ: 11.25(1H,s), 11.18(1H, s), 8.43(1H,s),8.07(6H,m), 8.01(1H,q),7.93(2H,m),7.68(1H, q),3.78(2H,dd),3.49(3H,s),3.15(2H,d),1.80(3H,s); Yield: 49%

EXAMPLE 38

S-[4-(N-{2-[N-(5-chloro(2-pyridyl))carbamoyl]-4-chlorophenyl}carbamoyl)phenyl]-S-methyl-N-[2-(4-pyridylthio)-acetyl]sulfoximide $^1$H NMR(DMSO-d6,400 MHz)δ: 11.26(1H,s),11.19(1H, s),8.43(1H,d),8.36(2H,m), 8.04(6H,m),7.96(2H,m),7.66 (1H,d),7.21(2H,d),3.96(2H,s),3.53 (3H,s); Yield=50%

EXAMPLE 39

S-[4-(N-{2-[N-(5-chloro(2-pyridyl))carbamoyl]-4-chlorophenyl}carbamoyl)phenyl]-S-methyl-N-(2-dimethylamino-acetyl)sulfoximide To a stirring solution of S-[4-(N-{2-[N-(5-chloro(2-pyridyl))carbamoyl]-4-chlorophenyl}carbamoyl)phenyl]-S-methyl-N-chloroacetyl sulfoximide (100 mg, 0.185 mmol, Example 6) in DMF (0.2 mL) was added 50% aqueous dimethylamine solution (164 mg, 0.162 mmol) followed by catalytic amount of KI. The reaction mixture was stirred at 25-30° C. for 12 hr and then diluted with water (5 mL). Filtration and drying afforded 50 mg of titled compound in 49% yield.

$^1$H NMR(DMSO-d6,400 MHz)δ: 11.21(2H,bs),8.4(1H,s), 8.1(6H,t)8.0(2H,d), 7.6(1H,s), 3.4(3H,s),2.88(2H,s),2.18 (6H,s).

Using appropriate starting materials and suitable modifications of the process described in Example 39, including suitable addition and/or deletion of steps as may be necessary, well within the scope of a person skilled in the art, the following compounds were prepared in an analogous manner.

EXAMPLE 40

S-[4-(N-{2-[N-(5-chloro(2-pyridyl))carbamoyl]-4-methoxyphenyl}carbamoyl)phenyl]-S-methyl-N-(2-dimethylamino-acetyl)sulfoximide $^1$H NMR (DMSO-d6, 400 MHz)δ: 11.098(1H,s),10.96 (1H,s),8.42(1H,d),8.12(5H,m), 7.94 (2H,d),7.39(1H,d),7.16 (1H,d),3.84(3H,s),3.28(3H,s),2.65(2H,s),1.22(6H,s); Yield=25%

EXAMPLE 41

S-(2-[4-(N-{2-[N-(5-chloro-2-pyridyl)carbamoyl]-4-chlorophenyl}carbamoyl)phenyl]-phenyl)-S-methyl-N-(2-dimethylamino-acetyl)sulfoximide $^1$H NMR (DMSO-d6, 400 MHz)δ: 11.3(1H,s), 11.25(1H, s), 8.45(1H,d), 8.44(1H,d), 7.94(2H,m),7.77(4H,m),7.74 (2H,m),7.45(1H,d),7.40(2H,d),7.38(1H,d),3.22(3H,s), 2.87 (2H,m),2.31(6H,s); Yield: 33%

EXAMPLE 42

S-[4-(N-{2-[N-(5-chloro(2-pyridyl))carbamoyl]-4-chlorophenyl}carbamoyl)phenyl]-S-methyl-N-(2-diethylamino-acetyl)sulfoximide $^1$H NMR (DMSO-d6, 400 MHz)δ: 11.27(1H,s), 11.2(1H, s),8.4(1H,dd)8.1(6H,m), 7.9(2H,m),7.6(1H,d),3.2(3H,s),3.2 (2H,s),2.4(4H,q),0.94(6H,t); Yield=66%

EXAMPLE 43

S-(2-[4-(N-{2-[N-(5-chloro-2-pyridyl)carbamoyl]-4-chlorophenyl}carbamoyl)phenyl]-phenyl)-S-methyl-N-(2-diethylamino-acetyl)sulfoximide $^1$H NMR(DMSO-d6,400 MHz)δ: 11.29(2H,bs),8.44(1H, d),8.27(1H,d),8.11(2H,m), 7.94(4H,m),7.77(2H,m),7.72 (1H,d),7.47(2H,d),7.38(1H,d),3.21(3H,s),2.97(2H,s), 2.49 (4H,m),0.89(6H,t); Yield: 88%

EXAMPLE 44

S-[4-(N-{2-[N-(5-chloro(2-pyridyl))carbamoyl]-4-methoxyphenyl}carbamoyl)phenyl]-S-methyl-N-(2-diethylamino-acetyl)sulfoximide ¹H NMR (DMSO-d6, 400 MHz)δ: 11.099(1H,s), 10.96 (1H,s), 8.41(1H,d), 8.09(5H,m), 7.93(2H,d), 7.39(1H,d), 7.17(1H,d), 3.87(3H,s),3.47(3H,s),3.218(2H,s),2.3(4H,m), 0.92(6H,m); Yield=44%

EXAMPLE 45

S-[4-(N-{2-[N-(5-chloro(2-pyridyl))carbamoyl]-4-chlorophenyl}carbamoyl)phenyl]-S-methyl-N-[2-(Methyl-propyl-amino)acetyl]sulfoximide ¹H NMR (DMSO-d6, 400 MHz)δ: 8.42(1H,d),8.13(6H, m),7.93(2H,m),7.68(1H,d), 3.48(3H,s),3.29(2H,s),2.34(2H, m),2.3(3H,s),1.36(2H,m),0.82(3H,m); Yield=78%

EXAMPLE 46

S-(2-[4-(N-{2-[N-(5-chloro-2-pyridyl)carbamoyl]-4-chlorophenyl}carbamoyl)phenyl]-phenyl)-S-methyl-N-[2-(methyl-propyl-amino)-acetyl]sulfoximide ¹H NMR (DMSO-d6, 400 MHz)δ: 8.44(1H,d),8.43(1H,d), 8.22(2H,m),7.94(4H,m), 7.79(2H,m),7.76(1H,d),7.38(2H, d),7.29(1H,d),3.17(3H,s),2.81(2H,d),2.24(2H,m), 2.1(3H,s), 1.12(2H,m),0.74(3H,t); Yield: 78%

EXAMPLE 47

S-[4-(N-{2-[N-(5-chloro(2-pyridyl))carbamoyl]-4-chlorophenyl}carbamoyl)phenyl]-S-methyl-N-(2-diisopropylamino-acetyl)sulfoximide ¹H NMR (DMSO-d6, 400 MHz)δ: 8.42(1H,d), 8.17(4H, m),8.05(2H,d),7.93(2H,m), 7.89(1H,d),3.45(3H,s),3.16(2H, s),1.15(2H,m),0.9(12H,d); Yield=86%

EXAMPLE 48

S-[4-(N-{2-[N-(5-chloro(2-pyridyl))carbamoyl]-4-chlorophenyl}carbamoyl)phenyl]-S-methyl-N-[2-(Carbamoylmethyl-methyl-amino)-acetyl]sulfoximide ¹H NMR (DMSO-d₆, 400 MHz)δ: 11.26(1H,s), 11.18(1H, s),8.43(1H,d),8.42(6H,m), 7.94(1H,47.22(1H,s),7.09(1H,s), 3.49(3H,s),3.286(2H,s),3.00(2H,s),2.313(3H,s); Yield=36%

EXAMPLE 49

S-(2-[4-(N-{2-[N-(5-chloro-2-pyridyl)carbamoyl]-4-chlorophenyl}carbamoyl)phenyl]-phenyl)-S-methyl-N-[2-(carbamoylmethyl-methyl-amino)-acetyl]sulfoximide ¹H NMR(DMSO-d6, 400 MHz)≠7: 11.27(2H,d),8.44(1H, d),8.43(1H,d),8.22(2H,m), 7.94(4H,m),7.79(2H,m),7.76 (1H,d),7.38(2H,d),7.30(1H,d),7.2(2H,d),3.21(3H,s), 2.96 (4H,m),2.24(3H,s); Yield: 92%

EXAMPLE 50

S-[4-(N-{2-[N-(5-chloro(2-pyridyl))carbamoyl]-4-chlorophenyl}carbamoyl)phenyl]-S-methyl-N-[(2-pyrrolidin-1-yl)-acetyl]sulfoximide ¹H NMR (DMSO-d₆, 400 MHz)δ: 11.18(1H,s), 11.132 (1H,S),8.43(1H,d),8.12(4H,m), 8.05(2H,d),7.93(2H,m),7.63 (1H,d),3.50(3H,s),3.21(2H,42.4(4H,t),1.7(4H,t);Yield=69%

EXAMPLE 51

S-(2-[4-(N-{2-[N-(5-chloro-2-pyridyl)carbamoyl]-4-chlorophenyl}carbamoyl)phenyl]-phenyl)-S-methyl-N-[(2-pyrrolidin-1-yl)-acetyl]sulfoximide ¹H NMR(DMSO-d6,400 MHz)δ: 11.27(2H,s),8.427(1H, d),8.34(1H,d),8.15(2H,m), 8.12(2H,d),8(1H,d),7.9(1H,dd), 7.895(2H,m),7.6(1H,dd),7.55(2H,d),7.39(1H,dd),3.3(3H,s), 2.9(2H,s),2.49(4H,m),1.79(4H,m); Yield: 93%

EXAMPLE 52

S-[4-(N-{2-[N-(5-chloro(2-pyridyl))carbamoyl]-4-chlorophenyl}carbamoyl)phenyl]-S-methyl-N-[(2-piperidin-1-yl)-acetyl]sulfoximide ¹H NMR(DMSO-d6, 400 MHz)δ: 11.28(1H,s),11.20(1H, S),8.43(1H,d),8.12 (6H,m), 7.9(2H,d),7.6(1H,d),3.48(3H,s), 3.01(2H,s),2.3(4H,t),1.42(4H,m),1.22(2H,m); Yield=91%

EXAMPLE 53

S-(2-[4-(N-{2-[N-(5-chloro-2-pyridyl)carbamoyl]-4-chlorophenyl}carbamoyl)phenyl]-phenyl)-S-methyl-N-[(2-piperidin-1-yl)-acetyl]sulfoximide ¹H NMR(DMSO-d6,400 MHz)δ: 11.29(1H,s)11.26(1H, s),8.44(1H,d),8.26(1H,d) 8.11(2H,m)7.95(4H,m),7.78(2H, m)7.73(1H,d),7.49(2H,d),7.39(1H,d)3.19(3H,s)2.71(2H,m) 2.31(4H,m)1.39(6Hm); Yield: 93%

EXAMPLE 54

S-[4-(N-{2-[N-(5-chloro(2-pyridyl))carbamoyl]-4-chlorophenyl}carbamoyl)phenyl]-S-methyl-N-[2-(4-hydroxypiperidinyl)-acetyl]sulfoximide ¹H NMR (DMSO-d6, 400 MHz)δ: 11.22(2H,bs), 8.34(1H, t), 8.08(6H,m),7.94(2H,m), 7.65(1H,d),4.48(1H,s),3.48(3H, s),3.35(1H,bs)3.08(2H,bd),2.66(2H,bt),2.15(2H,bs), 1.63 (2H,bd),1.32(2H,bd); Yield=75%

EXAMPLE 55

S-[4-(N-{2-[N-(5-chloro(2-pyridyl))carbamoyl]-4-chlorophenyl}carbamoyl)phenyl]-S-methyl-N-[2-(4-aminopiperidinyl)-acetyl]sulfoximide Prepared using Piperidin-4-yl-carbamic acid tert-butyl ester. Product obtained was deprotected with TFA to give titled compound in 34% yield.

¹H NMR (DMSO-d6,400 MHz)δ: 8.53(1H,d),8.42(3H,t), 8.24(1H,d),8.00(3H,m), 7.86(1H,dd), 7.44(1H,dd),3.49(3H, s),3.14(2H,s),2.81 (3H,bt),2.17(2H,bq), 1.72(2H,bd),1.41 (2H,bm).

EXAMPLE 56

S-(2-[4-(N-{2-[N-(5-chloro-2-pyridyl)carbamoyl]-4-chlorophenyl}carbamoyl)phenyl]-phenyl)-S-methyl-N-[2-(4-aminopiperidinyl)-acetyl]sulfoximide Prepared using Piperidin-4-yl-carbamic acid tert-butyl ester. Product obtained was deprotected with TFA to give titled compound in 76% yield.

¹H NMR(DMSO-d6,400 MHz)δ: 8.54(1H,d),8.39(1H,d), 8.19(3H,m),8.12(1H,dd), 8.03(1H,d), 7.80(3H,m), 7.47(1H, dd), 7.44 (2H,d),7.40(1H,dd),3.17(3H,s),2.81(2H,d), 2.66 (3H,m),2.05(2H,t),1.63(2H,t), 1.3(2H,t).

EXAMPLE 57

S-[4-(N-{2-[N-(5-chloro(2-pyridyl))carbamoyl]-4-chlorophenyl}carbamoyl)phenyl]-S-methyl-N-[2-(4-carbamoylpiperidinyl)-acetyl]sulfoximide ¹H NMR(DMSO-d6,400 MHz)δ: 11.26(1H,s)11.17(1H, S),8.43(1H,d),8.16(6H,m), 7.96(2H,m),7.66(1H,d),7.18(1H, s),6.69(1H,s),3.48(3H,s),2.79(2H,s),2.71(1H,m), 2.04(4H, m),1.5(4H,m);Yield=42%

EXAMPLE 58

S-[4-(N-{2-[N-(5-chloro(2-pyridyl))carbamoyl]-4-chlorophenyl}carbamoyl)phenyl]-S-methyl-N-[2-(4-morpholinyl)-acetyl]sulfoximide ¹H NMR (DMSO-d$_6$, 400 MHz)δ: 11.25(1H,s), 11.18(1H, s),8.42(1H,s),8.08(6H,m), 7.94(2H,m),7.67(1H,d),3.67(4H, t),3.47(2H,s),2.64(3H,s),2.37(4H,t); Yield=60%

EXAMPLE 59

S-[4-(N-{2-[N-(5-chloro(2-pyridyl))carbamoyl]-4-chlorophenyl}carbamoyl)phenyl]-S-methyl-N-[2-(4-methyl-piperazinyl)-acetyl]sulfoximide ¹H NMR(DMSO-d6,400 MHz)δ: 11.25(2H,bs),8.43(1H, dd),8.09(6H,m),7.93(2H,m), 7.64 (1H,d),3.47(2H,s),2.64 (3H,s),2.46(8H,m),2.27(3H,s); Yield=60%

EXAMPLE 60

S-(2-[4-(N-{2-[N-(5-chloro-2-pyridyl)carbamoyl]-4-chlorophenyl}carbamoyl)phenyl]-phenyl)-S-methyl-N-[2-(4-methylpiperazinyl)-acetyl]sulfoximide ¹H NMR (DMSO-d6, 400 MHz)δ: 11.28(2H,bs),8.45(1H, d),8.30(1H,d),8.11(2H,m), 7.94(4H,m),7.77(2H,m),7.72 (1H,d),7.47(2H,d),7.26(1H,d),3.57(2H,s),3.19(3H,s),2.87 (4H, m),2.48(4H,m),2.23(3H,s); Yield: 54%

EXAMPLE 61

S-[4-(N-{2-[N-(5-chloro(2-pyridyl))carbamoyl]-4-chlorophenyl}carbamoyl)phenyl]-S-methyl-N-[2-(4-methyl-homopiperazinyl)-acetyl]Sulfoximide ¹H NMR(DMSO-d6,400 MHz)δ: 11.25(2H,bs),8.34(1H, d),8.16(4H,m),8.05(2H,m), 7.93(2H,m),7.60(1H,bd),3.47 (3H,s),2.71(4H,bm),2.57(4H,bm),2.29(3H,s),1.68,(2H,bt); Yield=11%

EXAMPLE 62

S-[4-(N-{2-[N-(5-chloro(2-pyridyl))carbamoyl]-4-chlorophenyl}carbamoyl)phenyl]-S-methyl-N-[2-(piperazin-1-yl)-acetyl]sulfoximide Compound obtained by using N-Boc piperazine was deprotected using TFA to get desired product in 78% yield.

¹H NMR(DMSO-d6,400 MHz)δ: 8.43(1H,d),8.29(3H,m), 8.17(1H,d), 8.05(2H,d), 7.95(1H,d), 7.90(1H,m), 7.54(1H,t), 3.56(3H,s),3.15(2H,s), 2.79(4H,t),2.52(2H,m).

EXAMPLE 63

S-(2-[4-(N-{2-[N-(5-chloro-2-pyridyl)carbamoyl]-4-chlorophenyl}carbamoyl)phenyl]-phenyl)-S-methyl-N-[2-(piperazin-1-yl)-acetyl]sulfoximide ¹H NMR(DMSO-d6, 400 MHz)δ: 8.42(2H,m),8.38(2H, m),8.01(2H,m),7.91(1H,d), 7.89(1H,dd),7.78(2H,m),7.62 (1H,d),7.6(2H,dd),7.38(1H,d),3.31(3H,s),2.81(2H,d), 2.68 (4H,m),2.23(4H,m); Yield: 79%

EXAMPLE 64

S-[4-(N-{2-[N-(5-chloro(2-pyridyl))carbamoyl]-4-chlorophenyl}carbamoyl)phenyl]-S-methyl-N-[2-(3-oxo-piperazin-1-yl)-acetyl]sulfoximide ¹H NMR (DMSO-d6, 400 MHz)δ: 11.25(1H,s),11.18(1H, s),8.42(1H,d),8.09(6H,m), 7.95(2H,m),7.66(2H,m),3.05 (3H,s),3.27(2H,s),3.09(2H,t),3.04(2H,s),2.66(2H,t); Yield=67%

EXAMPLE 65

S-[4-(N-{2-[N-(5-chloro(2-pyridyl))carbamoyl]-4-chlorophenyl}carbamoyl)phenyl]-S-methyl-N-[2-(imidazol-1-yl)-acetyl]sulfoximide ¹H NMR(DMSO-d6,400 MHz)δ: 11.26(1H,s),11.18(1H, s),8.4(1H,dd),8.1(6H,m), 7.9(1H,dd),7.8(1H,d),7.6(2H,m), 7.0(1H,t),6.8(1H,s),4.8(2H,s),3.5(3H,s); Yield=20%

EXAMPLE 66

S-(2-[4-(N-{2-[N-(5-chloro-2-pyridyl)carbamoyl]-4-chlorophenyl}carbamoyl)phenyl]-phenyl)-S-methyl-N-[2-(imidazol-1-yl)-acetyl]sulfoximide ¹H NMR(DMSO-d6,400 MHz)δ: 11.27(2H,bs),8.42(1H, d),8.26(1H,d),8.14(1H,d), 8.09(1H,d), 7.99(2H,dd), 7.94(1H,d), 7.86(1H,d), 7.78(2H,m),7.67(1H,d),7.61(1H,s), 7.51 (2H,d),7.42(1H,d),7.05(1H,s),6.8(1H,s),4.63(1H,d), 4.48(1H,d),3.26(3H,s); Yield: 25%

EXAMPLE 67

S-[4-(N-{2-[N-(5-chloro(2-pyridyl))carbamoyl]-4-chlorophenyl}carbamoyl)phenyl]-S-methyl-N-[2-(1,2,4 Triazol-1-yl)-acetyl]sulfoximide ¹H NMR(DMSO-d₆, 400 MHz)δ:11.28(1H,s),11.17(1H,s),8.4(2H,t,),8.1(6H,d), 7.9(3H,t),7.8(1H,s),5.0(2H,s),3.5(3H,s); Yield=17%

EXAMPLE 68

Preparation of S-[4-(N-{2-[N-(5-chloro(2-pyridyl))carbamoyl]-4-chlorophenyl}carbamoyl)phenyl]-S-methyl-N-[(N-methoxy-N-methyl)-carbamoyl]sulfoximide To a stirring suspension of S-[4-(N-{2-[N-(5-chloro(2-pyridyl))carbamoyl]-4-chlorophenyl}carbamoyl)phenyl]-S-methyl sulfoximide (500 mg, 0.00108 mol) in pyridine (4 mL) was added methoxymethylcarbamoyl chloride (0.4 g, 0.00324 mol) at 0-5° C. under nitrogen atmosphere. Reaction mixture was stirred at 25-30° C. for 15 hr and then quenched in cold dilute HCl. Product obtained was extracted in DCM (50 mL). Organic layer was dried, evaporated and column purified using 1% methanol in chloroform and 230-400 mesh silica gel to get 350 mg titled product.

¹H NMR (CDCl₃, 400 MHz)δ: 11.96 (1H,s), 8.85(1H,d), 8.63(1H,s),8.26(2H,m 8.16(4H,m),7.80(1H,dd),7.74(1H,d), 7.58(1H,dd),3.76(3H,s),3.40(3H,s),3.21(3H,s); Yield: 59%

EXAMPLE 69

Preparation of S-[4-(N-{2-[N-(5-chloro(2-pyridyl))carbamoyl]-4-chlorophenyl}carbamoyl)phenyl]-S-methyl-N-[(N-hydroxy-N-methyl)-carbamoyl]sulfoximide To a stirring suspension of S-[4-(N-{2-[N-(5-chloro(2-pyridyl))carbamoyl]-4-chlorophenyl}carbamoyl)phenyl]-S-methyl-N-[(N-methoxy-N-methyl)-carbamoyl]sulfoximide (200 mg, 0.3642 mmol, product of example 68) in DCM (5 mL) was added 1M Boron tribromide solution in DCM (137 mg, 0.546 mmol) at −40 to −50° C. under nitrogen atmosphere. Reaction mixture was stirred at 25-30° C. for 2 hr and then quenched in cold water. Product obtained was extracted in DCM (50 mL).Organic layer was dried, evaporated and column purified using 1.5% methanol in chloroform and 230-400 mesh silica gel to get 100 mg of titled product;

¹H NMR(DMSO-d6,400 MHz)δ: 11.25(1H,s),11.19(1H,s),9.14(1H,s),8.43(1H,d), 8.08(6H,m),7.93(2H,m),7.66(1H,dd),3.32(3H,s); Yield: 51%

Using appropriate starting materials and suitable modifications of the process described in Example 68, including suitable addition and/or deletion of steps as may be necessary, well within the scope of a person skilled in the art, the following compounds were prepared in an analogous manner. Carbamoyl chlorides required for synthesis were prepared according to procedure given in *Chem. Pharm. Bull.* 55(2) 328-333 (2007).

Based on the above, the following compounds were prepared by suitable modifications/alterations as necessary.

EXAMPLE 70

S-[4-(N-{2-[N-(5-chloro(2-pyridyl))carbamoyl]-4-chlorophenyl}carbamoyl)phenyl]-S-methyl-N-[(2-hydroxy-ethyl)-methyl-carbamoyl]sulfoximide ¹H NMR(CDCl₃,400 MHz)δ: 8.86(1H,s),8.67(2H,d),8.32(1H,s),8.18(2H,m), 7.79(2H,m), 7.61 (2Hm,),7.35,(1H,m), 7.23(1H,m),3.81(2H,bs),3.72(2H,bs),3.45(3H,s),3.18(3H,s). Yield=52%

EXAMPLE 71

S-[4-(N-{2-[N-(5-chloro(2-pyridyl))carbamoyl]-4-chlorophenyl}carbamoyl)phenyl]-S-methyl-N-[(4-methylpiperazin-1-yl)-carbonyl]sulfoximide ¹HNMR(CDCl₃, 400 MHz)δ: 11.94(1H,s),8.85(1H,d), 8.67(1H,s),8.30(2H,m),8.13 (2H,dd), 7.79(2H,dd),7.61(1H,dd),3.72(2H,bs),3.55 (2H,bs),3.36(3H,s),2.40(4H,bs),2.35(3H,s); Yield=47%

EXAMPLE 72

Preparation S-[4-(N-{2-[N-(5-chloro(2-pyridyl))carbamoyl]-4-chlorophenyl}carbamoyl)phenyl]-S-methyl-N-(carbamoylmethyl)sulfoximide To a stirring solution of S-[4-(N-{2-[N-(5-chloro(2-pyridyl))carbamoyl]-4-chlorophenyl}carbamoyl)phenyl]-S-methyl sulfoximide (500 mg, 0.00108 mol) in DMF(2.5 mL) was added Sodium hydride (170 mg, 0.0036mol) at 25-30° C. under nitrogen atmosphere. Reaction mixture was stirred at 40-45° C. for 3 hr. Reaction mixture was cooled to 0-5° C. and to this was added iodoacetamide (240 mg, 0.0013 mol) and stirred for 12 hr at 25-30° C. Subsequent work up and column purification (100-200 mesh silica gel, 2% methanol in chloroform) gave 90 mg of titled product in 16% yield.

¹H NMR(DMSO-d6,400 MHz)δ: 11.24 (2H,bs),8.4 (1H,d),8.11 (6H,m),7.94(2H,m), 7.67(1H,d),7.2(2H,d),3.3 (3H,s),3.12(2H,s);

EXAMPLE 73

Preparation of S-[4-(N-{2-[N-(5-chloro(2-pyridyl))carbamoyl]-4-chlorophenyl}carbamoyl)phenyl]-S-methyl-N-[2-hydroxy-ethyl]sulfoximide Step 1: Preparation of S-[4-(N-{2-[N-(5-chloro(2-pyridyl))carbamoyl]-4-chloro phenyl}carbamoyl)phenyl]-S-methyl-N-(ethoxycarbonyl methyl)sulfoximide Prepared using Ethyl indo acetate insteaed of iodoacetamide with similar procedure as that of Example 72. Crude material is used for next step.

Step 2: Preparation of S-[4-(N-{2-[N-(5-chloro(2-pyridyl))carbamoyl]-4-chlorophenyl}carbamoyl)phenyl]-S-methyl-N-[2-hydroxy-ethyl]sulfoximide To a stirring solution of S-[4-(N-{2-[N-(5-chloro(2-pyridyl))carbamoyl]-4-chlorophenyl}carbamoyl)phenyl]-S-methyl-N-(ethoxycarbonyl methyl)sulfoximide (1.3 g, 0.00237 mol) in DMSO (4 mL) was added Sodium borohydride (360 mg, 0.00948 mol) at 60° C. in several lots. Reaction mixture was stirred at same temperature for 5 hr. Subsequent work up and column purification (100-200 mesh silica gel, 2% methanol in chloroform) gave 400 mg of titled product in 80% yield.

$^1$H NMR(DMSO-d6,400 MHz)δ: 11.25(1H, s), 11.17(1H, s),8.43(1H,dd),8.08(4H,m), 7.99(2H,m),7.95(1H,d),7.91 (1H,dd), 7.67(1H,dd),4.41(1H,t)3.33(2H,m),3.17(3H,s), 2.84(1H,m),2.712(1H,m);

EXAMPLE 74

S-[4-(N-{2-[N-(5-chloro(2-pyridyl))carbamoyl]-4-chlorophenyl}carbamoyl)phenyl]-S-methyl-N-(2-(diethylamino)ethyl)sulfoximide Step 1: Preparation of S-[4-(N-{2-[N-(5-chloro(2-pyridyl))carbamoyl]-4-chlorophenyl}carbamoyl) phenyl]-S-methyl-N-[2-bromo-ethyl]sulfoximide To a stirring suspension of S-[4-(N-{2-[N-(5-chloro(2-pyridyl))carbamoyl]-4-chlorophenyl}carbamoyl)phenyl]-S-methyl-N-[2-hydroxy-ethyl]sulfoximide (0.6 g, 0.00118 mol) in DCM (6 mL) was added triphenyl phosphine (460 mg, 0.00177 mol) followed by carbon tetrabromide (589 mg, 0.00177 mol) at 25-30° C. Reaction mixture was stirred at same temperature for 3 hr. Subsequent work up and column purification (100-200 mesh silica gel, 10-50% ethyl acetate in hexane) gave 300 mg of titled product.

Step 2: Preparation of S-[4-(N-{2-[N-(5-chloro(2-pyridyl))carbamoyl]-4-chlorophenyl}carbamoyl) phenyl]-S-methyl-N-(2-(diethylamino)ethyl)sulfoximide To a stirring solution of S-[4-(N-{2-[N-(5-chloro(2-pyridyl))carbamoyl]-4-chlorophenyl}carbamoyl)phenyl]-S-methyl-N-[2-bromo-ethyl]sulfoximide (150 mg, 0.00026 mol) in DMF(0.7 mL) was added diethyl amine (1 mL) at 25° C. Reaction mixture was stirred at same temperature for 2 hr. Reaction mixture was diluted with water and filtered. Drying afforded 85 mg of titled compound in 60% yield.

$^1$H NMR(CDCl$_3$,400 MHz)δ:11.93(1H,s),8.8(1H,d),8.85 (2H,dd)8.3(2H,d),8.2(2H,d) 8.0(2H,t)7.95(1H,s)7.7(1H,d) 3.1(31-1,s)3.0(1H,m)2.95(1H,m)2.67(2H,t)2.5(4H,m), 1.1 (6H,t).

Using appropriate starting materials and suitable modifications of the process described in Example 74, including suitable addition and/or deletion of steps as may be necessary, well within the scope of a person skilled in the art, the following compounds were prepared in an analogous manner.

EXAMPLE 75

S-[4-(N-{2-[N-(5-chloro(2-pyridyl))carbamoyl]-4-chlorophenyl}carbamoyl)phenyl]-S-methyl-N-(2-(pyrrolidin-1-yl)ethyl)sulfoximide $^1$H NMR(CDCl$_3$,400 MHz)δ:12.0(1H, s),8.8(1H,d),8.3 (2H,d,),8.1(3H,t),7.8(2H,t), 7.5 (2H,t),7.5(1H,dd),2.64(3H, s),2.40(2H,t),2.20(6H,m),1.64(4H,t); Yield=64%

EXAMPLE 76

S-[4-(N-{2-[N-(5-chloro(2-pyridyl))carbamoyl]-4-chlorophenyl}carbamoyl)phenyl]-S-methyl-N-[2-dimethylamino-ethyl]sulfoximide $^1$H NMR(DMSO-d6,400 MHz)δ: 11.23(2H,bs), 8.42(1H, m),8.13(4H,m), 7.98(2H,m), 7.918(2H,m),7.62(1H,m) 3.17 (3H,s),2.92(1H,m),2.87(1H,m),2.68(2H,m),2.15(6H,s); Yield: 26%

EXAMPLE 77

S-[4-(N-{2-[N-(5-chloro(2-pyridyl))carbamoyl]-4-chlorophenyl}carbamoyl)phenyl]-S-methyl-N-[(2-(2-hydroxyethyl)-methyl-amino)-ethyl]sulfoximide $^1$H NMR (DMSO-d6, 400 MHz)δ: 8.42 (1H,d),8.14(4H, m),7.93(4H,m),7.61(1H,m),4.31(1H,s),3.55(2H,m),3.2(3H, s),2.91(2H,m),2.87(1H,s),2.11(3H,s); Yield: 22%

EXAMPLE 78

S-[4-(N-{2-[N-(5-chloro(2-pyridyl))carbamoyl]-4-chlorophenyl}carbamoyl)phenyl]-S-methyl-N-[2-(4-methylpiperazin-1-yl)-ethyl]sulfoximide $^1$H NMR (DMSO-d6, 400 MHz)δ: 11.23(2H,bs),8.42(1H, d),8.10(4H,m),7.95(4H,m), 7.65(1H,m),3.16(3H,S),2.46 (8H,m), 2.40(2H,t),2.27(3H,s),1.40(2H,t); Yield: 12%

EXAMPLE 79

S-[4-(N-{2-[N-(5-chloro(2-pyridyl))carbamoyl]-4-chlorophenyl}carbamoyl)phenyl]-S-methyl-N-[2-(4-morpholinyl)-ethyl]sulfoximide $^1$H NMR(DMSO-d6,400 MHz)δ: 8.42(1H,d)8.111(4H, m),7.93 (2H,m) 7.91(2H,m), 7.64(1H,m), 3.47(4H,m),3.16 (3H,S),2.91(2H,m),2.38(2H,m),2.29(4H,m); Yield: 38%

EXAMPLE 80

Preparation of S-[4-(N-{2-[N-(5-chloro(2-pyridyl)) carbamoyl]-4-chlorophenyl}carbamoyl)phenyl]-S-methyl-N-[2-(4-methyl-homopiperazinyl)-ethyl] sulfoximide $^1$H NMR(CDCl$_3$,400 MHz)δ:12.26(1H,s),8.87(1H,d), 8.72(1H,bs),8.65(2H,dd),8.32(2H,d),8.07(2H,d),7.78(1H, dd),7.80(1H,d),7.78(1H,d),2.64(3H,s),2.46(6H,m),2.36(4H, m), 2.27(3H,s),1.37(4H,m); Yield: 21%

EXAMPLE 81

Preparation of (−)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide Step 1: Preparation of S-[4-(N-{2-[N-(5-chloro(2-pyridyl))carbamoyl]-4-chlorophenyl}carbamoyl) phenyl]-S-methyl-N-(1-tert-butoxycarbonyl-pyrrolidin-2-carbonyl)sulfoximide To a stirring solution of S-[4-(N-{2-[N-(5-chloro(2-pyridyl))carbamoyl]-4-chlorophenyl}carbamoyl)phenyl]-S-methyl sulfoximide (4 g, 0.00868 mol) and Boc protected (L)-Proline (2.8 g, 0.01302 mol) in DMF (10 mL) was added EDCI (2.5 g, 0.01302 mol) followed by catalytic amount of DMAP. The reaction mixture was stirred at 25-30° C. for 4 hr and then diluted with water (50 mL). Product was filtered to get diasteromeric mixture of titled compound. Diastereomeric separation by column chromatography (230-400 mesh silica gel, 30-35% Ethyl acetate in Hexane) gave 1.2 g non-polar isomer and 1.3 g polar isomer.

$^1$H NMR(DMSO-d6,400 MHz)δ: 11.26(2H,bs),8.42(1H, bs),8.10(5H,bs),7.91(2H,bs), 7.64(1H,bs),6.91(1H,bs),3.71 (2H,s),3.61 (3H,s),1.33(9H,s).

Step 2: Preparation of (−)-S-[4-(N-{2-[N-(5-chloro (2-pyridyl))carbamoyl]-4-chlorophenyl}carbamoyl) phenyl]-S-methyl sulfoximide To a stirring solution of S-[4-(N-{2-[N-(5-chloro(2-pyridyl))carbamoyl]-4-chlorophenyl}carbamoyl)phenyl]-S-methyl-N-(1-tert-butoxycarbonyl-pyrrolidin-2-carbonyl) sulfoximide (1.2 g, 0.00182 mol, nonpolar isomer) in methanol (4 mL) was added conc. sulfuric acid (0.7 g, 0.00728 mol) at 5-10° C. The reaction mixture was stirred at 25-30° C. for 4 hr and then diluted with water. Product obtained was extracted in chloroform at 8-9 pH. Organic layer was dried and concentrated to give 640 mg of titled product in 63% yield.

Step 3: Preparation of (−)-S-[4-(N-{2-[N-(5-chloro (2-pyridyl))carbamoyl]-4-chlorophenyl}carbamoyl) phenyl]-S-methyl-N-chloroacetyl sulfoximide Prepared using similar procedure as that of example 6; Yield=77%

Step 4: Preparation of (−)-S-[4-(N-{2-[N-(5-chloro (2-pyridyl))carbamoyl]-4-chlorophenyl}carbamoyl) phenyl]-S-methyl-N-(2-diethylamino-acetyl)sulfoximide Prepared using similar procedure as that of Example 39;
$^1$H NMR (DMSO-d6,400 MHz)δ: 11.23 (2H,bs),8.42(1H, d),8.08(6H,m),7.92(2H,m), 7.66(1H,d),3.47(3H,s),3.24(2H, bs),2.54(4H,bd),0.92(6H,t); SOR=−42.01° at 25° C.(c=0.2% in DMSO); Yield=32%

EXAMPLE 82

Preparation of (+)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide Prepared using similar procedure as that of example 81 starting with 1.3 g of polar isomer obtained in Example 81, step 1.
$^1$H NMR(DMSO-d6,400 MHz)δ: 11.24(2H,b s),8.43(1H, d),8.08(6H,m),7.91(2H,m), 7.66(1H, d),3.48(3H, s),3.24 (2H,bs),2.54 (4H,bd),0.91(6H,t).
SOR=+39.35° at 25° C., C=0.2% in DMSO; Yield=46%

EXAMPLE 83

Preparation of S-[4-(N-{2-[N-(5-chloro(2-pyridyl)) carbamoyl]-4-chlorophenyl}carbamoyl)phenyl]-S-methyl-N-(2-diethylamino-acetyl)sulfoximide hydrochloride To a stirred solution of S-[4-(N-{2-[N-(5-chloro(2-pyridyl))carbamoyl]-4-chlorophenyl}carbamoyl)phenyl]-S-methyl-N-(2-diethylamino-acetyl)sulfoximide (200 mg,0.3478 mmol) in DCM (5mL) was added 12% ethereal hydrochloric acid solution (115 mg,0.3826 mmol) at 10-15° C. After one hour, solvent was concentrated and product was stirred in ether. Filteration afforded 90 mg of desired product in 42% yield.

$^1$H NMR (DMSO-d6, 400 MHz)δ: 11.27(1H,s), 11.24(1H, s), 9.28(1H,s),8.44(1H,d) 8.17(3H,m),8.10(2H,m),7.94(2H, m),7.69(2H,dd),4.07(2H, d),3.65(3H, s),3.06(4H,m), 1.15(6H,m).

EXAMPLE 84

Preparation of S-[4-(N-{2-[N-(5-chloro(2-pyridyl)) carbamoyl]-4-chlorophenyl}carbamoyl)phenyl]-S-{ (2-diethylamino)ethyl}sulfoximide Step 1 Preparation of 4-(2-Hydroxy-ethylsulfanyl)-benzoic acid To a stirred solution of 4-mercapto benzoic acid (10 g, 0.0645 mmol) in methanol (100 mL) was added KOH (10.8 g, 0.1935 mol) at 25-30° C. Chloroethanol (10.3 g, 0.1290 mol) was then added to it. Reaction mixture was refluxed for 4 hr. Excess methanol was evaporated and then quenched in dil.HCl. Product obtained was filtered. Drying afforded 8 g of titled compound in 62% yield.

Step 2 Preparation of 4-(2-Methoxy-ethylsulfanyl)-benzoic acid

To a stirred solution of 4-(2-Hydroxy-ethylsulfanyl)-benzoic acid (7 g, 0.0352 mol) in DMF (140 mL) was added Sodium hydride (4.2 g, 0.088 mmol) at 5-10° C. under nitrogen atmosphere. Reaction mixture was stirred for 15 min at 25-30° C. and then Methyl iodide (6.6 mL, 0.1057mol) was added to at 10-15° C. Stirring continued for 3 hr after removing cooling. Reaction mixture was then quenched in aqueous NaOH solution and stirred for 30 min. Aqueous layer was washed with ethyl acetate (200 mL). Aqueous layer was then acidified using dil.HCl. Product obtained was filtered which on drying afforded 4.5 g of desired product in 60% yield.

Step 3: Preparation of 4-(2-Methoxy-ethylsulfanyl)-benzoic acid methyl ester 4-(2-Methoxy-ethylsulfanyl)-benzoic acid was esterified in methanol by adding catalytic amount of sulfuric acid. Subsequent work up afforded 4 g of desired product in 78% yield.

Step 4: Preparation of 4-(2-Methoxy-ethanesulfinyl)-benzoic acid methyl ester

Prepared using similar procedure as that of Example 1 step 3 in 42% yield.

Step 5: Preparation of S-(4-methoxycarbonylphenyl)-S-(2-methoxyethyl)sulfoximide Prepared using similar procedure as that of Example 1 step 4 in 58% yield.

Step 6: Preparation of S-(4-methoxycarbonylphenyl)-S-(2-methoxyethyl)-N-benzyloxycarbonyl sulfoximide Prepared using similar procedure as that of Example 1 step 5 in 82% yield.

Step 7: Preparation of S-(4-carboxyphenyl)-S-(2-methoxyethyl)-N-benzyloxycarbonyl sulfoximide Prepared using similar procedure as that of Example 1 step 6 in 60% yield.

Step 8: Preparation of S-[4-(N-{2-[N-(5-chloro(2-pyridyl))carbamoyl]-4-chlorophenyl}carbamoyl)phenyl]-S-(2-methoxy ethyl)-N-benzyloxycarbonyl sulfoximide Prepared using similar procedure as that of Example 1 step 7 in 28% yield.

Step 9: Preparation of S-[4-(N-{2-[N-(5-chloro(2-pyridyl))carbamoyl]-4-chlorophenyl}carbamoyl)phenyl]-S-(2-hydroxy ethyl)-sulfoximide To a stirring solution of S-[4-(N-{2-[N-(5-chloro(2-pyridyl))carbamoyl]-4-chlorophenyl}carbamoyl)phenyl]-S-(2-methoxyethyl)-N-benzyloxycarbonyl sulfoximide (0.3 g, 0.00046 mol) in DCM (3 mL) was added 1M solution of $BBr_3$ in DCM(0.33 g, 0.00138 mol) at −70° C. under nitrogen atmosphere. Reaction mixture was stirred for 3 hr at 25-30° C. Subsequent work up and column purification (2% methanol in chloroform and 100-200 mesh silica gel) gave 65 mg of desired product in 28% yield.
$^1$H NMR (DMSO-$d_6$, 400 MHz)δ: 11.25(1H,s), 11.18(1H, s), 8.4(1H,d),8.13(2H,d), 8.10(4H,d,d,)8.0(1H,s),7.68(2H,0, 4.81(1H,t),4.47(1H,s),3.67(2H,t,)3.31(2H,t).

Step 10: Preparation of S-[4-(N-{2-[N-(5-chloro(2-pyridyl))carbamoyl]-4-chlorophenyl}carbamoyl)phenyl]-S-(2-hydroxy ethyl)-N-acetyl sulfoximide To a stirring solution of S-[4-(N-{2-[N-(5-chloro(2-pyridyl))carbamoyl]-4-chlorophenyl}carbamoyl)phenyl]-S-(2-hydroxy ethyl)-sulfoximide (0.550 g, 0.00111 mol) in DCM (10 mL) was added pyridine (0.131 g, 0.001665 mol) at 5-10° C. under nitrogen atmosphere followed acetyl chloride (0.105 g, 0.00134 mol). Reaction mixture was stirred for 3 hr at 25-30° C. Subsequent work up and column purification (55% ethyl acetate in hexane and 100-200 mesh silica gel) gave 100 mg of desired product in 17% yield.

Step 11: Preparation of S-[4-(N-{2-[N-(5-chloro(2-pyridyl))carbamoyl]-4-chlorophenyl}carbamoyl)phenyl]-S-(2-bromoethyl)-N-acetyl sulfoximide To a suspension of S-[4-(N-{2-[N-(5-chloro(2-pyridyl))carbamoyl]-4-chlorophenyl}carbamoyl)phenyl]-S-(2-hydroxy ethyl)-N-acetyl sulfoximide (90 mg, 0.000168 mol) in DCM (15 mL) was added triphenyl phosphine (44 mg, 0.000168 mol) with stirring followed by carbon tetrabromide (55 mg, 0.000168 mol) at 25-30° C. Reaction mixture was stirred at same temperature for 3 hr. Subsequent work up and column purification (100-200 mesh silica gel, 50% ethyl acetate in hexane) gave 50 mg of titled product in 50% yield.

Step 12: Preparation of S-[4-(N-{2-[N-(5-chloro(2-pyridyl))carbamoyl]-4-chlorophenyl}carbamoyl)phenyl]-S-{(2-diethylamino)ethyl}sulfoximide To a stirring solution of diethylamine (0.4 mL) was added S-[4-(N-{2-[N-(5-chloro(2-pyridyl))carbamoyl]-4-chlorophenyl}carbamoyl)phenyl]-S-(2-bromo ethyl)-N-acetyl sulfoximide (40mg, 0.000067 mol) at 25-30° C. Reaction mixture was stirred at same temperature for 0.5 hr. Reaction mixture was then poured in 0.5 ml conc. sulfuric acid and stirred for 3 hr. Subsequent work up gave 15 mg of titled product in 41% yield.
$^1$H NMR(DMSO-$d_6$,400 MHz)δ: 11.25(1H,s),11.17(1H, s),8.42(1H,d),8.12(2H,d) 8.04(4H,m),7.94(2H,m),7.67(1H, d),4.43(1H,bs),3.26(2H,t),2.68(2H,t),2.31(4H,q), 0.78(6H,t).

Activity Data:

In vitro Factor Xa inhibitory activities were determined as per standard protocols and the results of representative compounds are provided in tables 1 and 2 below as proof of the efficacies of the novel class of compounds disclosed above.

TABLE 1

| Example | % Factor Xa inhibition at 0.1 µM using chromogenic assay |
|---|---|
| 1 | 75 |
| 4 | 93 |
| 5 | 95 |
| 14 | 84 |
| 24 | 85 |
| 26 | 69 |
| 28 | 82 |
| 40 | 56 |
| 41 | 95 |
| 42 | 70 |
| 43 | 79 |
| 50 | 64 |
| 52 | 60 |
| 53 | 79 |
| 56 | 81 |
| 74 | 77 |
| 75 | 74 |
| 76 | 66 |

TABLE 2

| Example | PTCT2(Conc. required to double the prothrombin time using human plasma) µM |
|---|---|
| 4 | 4.1 |
| 5 | 0.69 |
| 40 | 1.2 |
| 41 | 1.9 |
| 42 | 0.7 |
| 50 | 0.68 |
| 74 | 1.23 |
| 75 | 0.98 |
| 76 | 1.14 |

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as anticoagulant compound suitable for humans and other warm blooded animals, and may be administered either by oral, topical or parenteral administration.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:
1. A compound of formula (I)

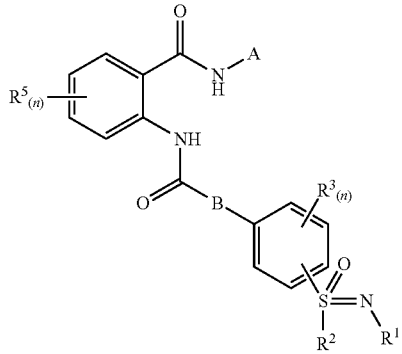

wherein
'A' represents an optionally substituted heterocyclic group;
'B' represents either a bond or B represents a radical of following formula

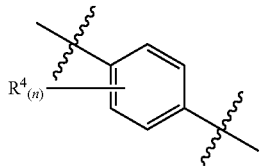

$R^2$ represents $(C_1-C_{10})$alkyl, $(C_3-C_{10})$cycloalkyl groups, wherein the $(C_1-C_{10})$alkyl chain further optionally contains from 1-3 heteroatoms selected from $NR_aR_b$, O, S or the groups carbonyl or iminocarbonyl; wherein either of $R_aR_b$ if present, is independently selected from H, $(C_1-C_3)$alkyl groups; provided that the chain forms other than S—S, S—O, or O—O bond;
$R^1$ represents hydrogen, cyano or the groups selected from optionally substituted $(C_1-C_{10})$alkyl groups wherein the alkyl group may optionally contain from 1-3 heteroatoms selected from $NR_aR_b$, O, S or the groups carbonyl or iminocarbonyl; wherein either of RaRb if present, is independently selected from H, $(C_1-C_3)$alkyl groups; provided that the chain forms other than S—S, S—O, or O—O bond; or $R^1$ represents
optionally substituted groups selected from $(C_3-C_{10})$cycloalkyl, halo$(C_1-C_6)$alkyl, $(C_1-C_6)$heteroaryl, $(C_1-C_6)$aryl, aralkyl, heterocycle, heteroarylalkyl, heterocyclylalkyl, acyl, aminoalkyl, hydroxyalkyl, alkoxyalkyl, aryloxyalkyl, aralkoxyalkyl, aminocarbonyl, alkoxycarbonyl, cycloalkylcarbonyl, heterocyclylcarbonyl, arylcarbonyl, aminosulfonyl and alkylsulfonyl derivatives; or $R^1$ represents the following groups,

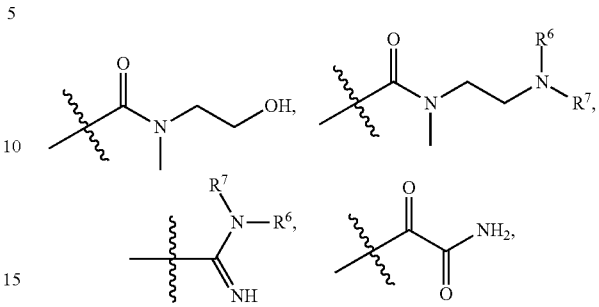

where, $R^6$ and $R^7$ are independently selected from hydrogen, $(C_1-C_6)$alkyl;
alternatively, $R^6$ and $R^7$ may cyclise to form a 5-7 membered heterocyclic ring; $R^3$, $R^4$ and $R^5$ may be same or different and at each occurrence independently represents hydrogen, hydroxyl, halo, thio, amino, nitro, or substituted or unsubstituted groups selected from $(C_1-C_6)$alkyl, $(C_1-C_6)$cycloalkyl, halo$(C_1-C_6)$alkyl, $(C_1-C_6)$alkoxy, heterocycleoxy, halo$(C_1-C_6)$alkoxy, alkylamino, aminoalkyl, mono, di or trisubstituted amino, hydroxyalkyl, alkoxyalkyl, alkylsulfonyl, alkylsulfonylamino, aminocarbonyl, and aminosulfonyl derivatives;
n represents integers from 1-4.

2. A compound as claimed in claim 1 wherein the $R^1$ is selected from hydrogen, cyano, optionally substituted groups selected from acyl, aminocarbonyl, $(C_1-C_{10})$ alkyl, aminoalkyl, hydroxyalkyl, heterocycle, heterocyclylalkyl groups.

3. A compound claimed in claim 1 wherein each of $R^3$, $R^4$, $R^5$ groups are independently selected from hydrogen, hydroxyl, halo, optionally substituted $(C_1-C_6)$alkyl, $(C_1-C_6)$alkoxy, heterocycleoxy, mono, di or trisubstituted amino groups.

4. A compound claimed in claim 1 wherein the substituents on 'A' are selected from halogen, hydrogen, hydroxy, optionally substituted amino, nitro, alkylamino, aminoalkyl, $(C_1-C_6)$alkyl, halo$(C_1-C_6)$alkyl, $(C_1-C_6)$alkoxy, aminocarbonyl, aminosulfonyl, and optionally substituted aminooxy derivatives.

5. A compound claimed in claim 1 wherein the substituents on $R^2$ are selected from hydrogen, hydroxyl, amino, $(C_1-C_6)$alkoxy, acyl, acylamino, alkylamino, aminoalkyl, mono, di or trisubstituted amino, alkylsulfonylamino, alkoxycarbonylamino, aminocarbonylamino, heterocycle, alkylsulfonyl, aminocarbonyl derivatives.

6. A compound claimed in claim 1 wherein the substituents on $R^1$ are selected from hydrogen, $(C_1-C_6)$alkyl, halogen, cyano, optionally substituted mono, di or trisubstituted amino, optionally substituted groups selected from carbocyclic or heterocyclic, $(C_1-C_6)$alkoxy, alkylsulfonyl, aminosulfonyl groups.

7. A compound claimed in claim 1 wherein the substituents on 'A' are selected from halogen, hydroxy, optionally substituted amino, aminoalkyl, $(C_1-C_6)$alkoxy, aminocarbonyl groups.

8. A compound claimed in claim 1 wherein the substituents on $R^2$ are selected from hydrogen, hydroxyl, mono, di or trisubstituted amino, $(C_1-C_6)$alkoxy groups.

9. A compound claimed in claim 1 wherein the substituents on $R^1$ are selected from hydrogen, halogen, cyano, optionally substituted groups selected from $(C_1-C_6)$alkyl, $(C_1-C_6)$ alkoxy, mono, di or trisubstituted amino, carbocyclic or heterocyclic groups.

10. A compound claimed in claim 1 selected from

S-[4-(N-{2-[N-(5-chloro(2-pyridyl))carbamoyl]-4-chlorophenyl}carbamoyl)phenyl]-S-methyl sulfoximide;

S-[4-(N-{2-[N-(5-chloro(2-pyridyl))carbamoyl]-4-methoxyphenyl}carbamoyl)phenyl]-S-methyl sulfoximide;

S-[4-(N-{2-[N-(5-chloro(2-pyridyl))carbamoyl]-4-chlorophenyl}carbamoyl)phenyl]-S-ethyl sulfoximide;

S-[4-(N-{2-[N-(5-chloro(2-pyridyl))carbamoyl]-4-chlorophenyl}carbamoyl)phenyl]-S-methyl-N-chloroacetyl sulfoximide;

S-[4-(N-{2-[N-(5-chloro(2-pyridyl))carbamoyl]-4-chlorophenyl}carbamoyl)phenyl]-S-methyl-N-acetyl sulfoximide;

S-[4-(N-{2-[N-(5-chloro(2-pyridyl))carbamoyl]-4-chlorophenyl}carbamoyl)phenyl]-S-methyl-N-propionyl sulfoximide;

S-[4-(N-{2-[N-(5-chloro(2-pyridyl))carbamoyl]-4-chlorophenyl}carbamoyl)phenyl]-S-methyl-N-cyclopropylcarbonyl sulfoximide;

S-[4-(N-{2-[N-(5-chloro(2-pyridyl))carbamoyl]-4-chlorophenyl}carbamoyl)phenyl]-S-methyl-N-methoxycarbonyl sulfoximide;

S-[4-(N-{2-[N-(5-chloro(2-pyridyl))carbamoyl]-4-chlorophenyl}carbamoyl)phenyl]-S-methyl-N-methanesulfonyl sulfoximide;

S-[4-(N-{2-[N-(5-chloro(2-pyridyl))carbamoyl]-4-chlorophenyl}carbamoyl)phenyl]-S-methyl-N-cyano sulfoximide;

S-[4-(N-{2-[N-(5-chloro(2-pyridyl))carbamoyl]-4-chlorophenyl}carbamoyl)phenyl]-S-methyl-N-carbamoyl sulfoximide;

S-[4-(N-{2-[N-(5-chloro(2-pyridyl))carbamoyl]-4-chlorophenyl}carbamoyl)phenyl]-S-methyl-N-(tert-butoxycarbonylamino-acetyl)sulfoximide;

S-[4-(N-{2-[N-(5-chloro(2-pyridyl))carbamoyl]-4-chlorophenyl}carbamoyl)phenyl]-S-methyl-N-aminocarbonylcarbonyl sulfoximide;

S-[4-(N-{2-[N-(5-chloro(2-pyridyl))carbamoyl]-4-chlorophenyl}carbamoyl)phenyl]-S-methyl-N-(4-pyridylcarbonyl)sulfoximide;

S-[4-(N-{2-[N-(5-chloro(2-pyridyl))carbamoyl]-4-chlorophenyl}carbamoyl)phenyl]-S-methyl-N-(4-piperidinylcarbonyl)sulfoximide;

S-[4-(N-{2-[N-(5-chloro(2-pyridyl))carbamoyl]-4-chlorophenyl}carbamoyl)phenyl]-S-methyl-N-(1-Ethyl-piperidine-4-carbonyl)sulfoximide;

S-[4-(N-{2-[N-(5-chloro(2-pyridyl))carbamoyl]-4-chlorophenyl}carbamoyl)phenyl]-S-methyl-N-(1-acetyl-piperidine-4-carbonyl)sulfoximide;

S-[4-(N-{2-[N-(5-chloro(2-pyridyl))carbamoyl]-4-chlorophenyl}carbamoyl)phenyl]-S-methyl-N-cyanoacetyl sulfoximide;

S-[4-(N-{2-[N-(5-chloro(2-pyridyl))carbamoyl]-4-chlorophenyl}carbamoyl)phenyl]-S-methyl-N-methoxyacetyl sulfoximide;

S-[4-(N-{2-[N-(5-chloro(2-pyridyl))carbamoyl]-4-methoxyphenyl}carbamoyl)phenyl]-S-methyl-N-methoxyacetyl sulfoximide;

S-[4-(N-{2-[N-(5-chloro(2-pyridyl))carbamoyl]-4-chlorophenyl}carbamoyl)phenyl]-S-ethyl-N-methoxyacetyl sulfoximide;

S-[4-(N-{2-[N-(5-chloro(2-pyridyl))carbamoyl]-4-chlorophenyl}carbamoyl)phenyl]-S-methyl-N-ethoxyacetyl sulfoximide;

S-[4-(N-{2-[N-(5-chloro(2-pyridyl))carbamoyl]-4-chlorophenyl}carbamoyl)phenyl]-S-methyl-N-(acetylamino-acetyl)sulfoximide;

S-[4-(N-{2-[N-(5-chloro(2-pyridyl))carbamoyl]-4-chlorophenyl}carbamoyl)phenyl]-S-methyl-N-[2-(4-pyridylthio)-acetyl]sulfoximide;

S-[4-(N-{2-[N-(5-chloro(2-pyridyl))carbamoyl]-4-chlorophenyl}carbamoyl)phenyl]-S-methyl-N-(2-dimethylamino-acetyl)sulfoximide;

S-[4-(N-{2-[N-(5-chloro(2-pyridyl))carbamoyl]-4-methoxyphenyl}carbamoyl)phenyl]-methyl-N-(2-dimethylamino-acetyl)sulfoximide;

S-[4-(N-{2-[N-(5-chloro(2-pyridyl))carbamoyl]-4-chlorophenyl}carbamoyl)phenyl]-S-methyl-N-(2-diethylamino-acetyl)sulfoximide;

S-[4-(N-{2-[N-(5-chloro(2-pyridyl))carbamoyl]-4-methoxyphenyl}carbamoyl)phenyl]-S-methyl-N-(2-diethylamino-acetyl)sulfoximide;

S-[4-(N-{2-[N-(5-chloro(2-pyridyl))carbamoyl]-4-chlorophenyl}carbamoyl)phenyl]-S-methyl-N-[2-(Methyl-propyl-amino)acetyl]sulfoximide;

S-[4-(N-{2-[N-(5-chloro(2-pyridyl))carbamoyl]-4-chlorophenyl}carbamoyl)phenyl]-S-methyl-N-(2-diisopropylamino-acetyl)sulfoximide;

S-[4-(N-{2-[N-(5-chloro(2-pyridyl))carbamoyl]-4-chlorophenyl}carbamoyl)phenyl]-S-methyl-N-[2-(Carbamoylmethyl-methyl-amino)-acetyl]sulfoximide;

S-[4-(N-{2-[N-(5-chloro(2-pyridyl))carbamoyl]-4-chlorophenyl}carbamoyl)phenyl]-methyl-N-[(2-Pyrrolidin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[(2-Piperidin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-hydroxypiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-aminopiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-carbamoylpiperidinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-morpholinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-methyl-piperazinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(4-methyl-homopiperazinyl)-acetyl]sulfoximide;

S-[4-(N-{2-[N-(5-chloro(2-pyridyl))carbamoyl]-4-chlorophenyl}carbamoyl)phenyl]-S-methyl-N-[2-(Piperazin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(3-Oxo-piperazin-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-amidazol-1-yl)-acetyl]sulfoximide;

S-[4-(N-{2-[N-(5-chloro(2-pyridyl))carbamoyl]-4-chlorophenyl}carbamoyl)phenyl]-S-methyl-N-[2-(1,2,4 Triazol-1-yl)-acetyl}sulfoximide;

S-[4-(N-{2-[N-(5-chloro(2-pyridyl))carbamoyl]-4-chlorophenyl}carbamoyl)phenyl]-S-methyl-N-[(N-methoxy-N-methyl)-carbamoyl]sulfoximide;
S-[4-(N-{2-[N-(5-chloro(2-pyridyl))carbamoyl]-4-chlorophenyl}carbamoyl)phenyl]-S-methyl-N-[(N-hydroxy-N-methyl)-carbamoyl]sulfoximide;
S-[4-(N-{2-[N-(5-chloro(2-pyridyl))carbamoyl]-4-chlorophenyl}carbamoyl)phenyl]-S-methyl-N-[(2-Hydroxy-ethyl)-methyl-carbamoyl]sulfoximide;
S-[4-(N-{2-[N-(5-chloro(2-pyridyl))carbamoyl]-4-chlorophenyl}carbamoyl)phenyl]-S-methyl-N-[(4-methylpiperazin-1-yl)-carbonyl]sulfoximide;
S-[4-(N-{2-[N-(5-chloro(2-pyridyl))carbamoyl]-4-chlorophenyl}carbamoyl)phenyl]-S-methyl-N-(carbamoylmethyl)sulfoximide;
S-[4-(N-{2-[N-(5-chloro(2-pyridyl))carbamoyl]-4-chlorophenyl}carbamoyl)phenyl]-S-methyl-N-[2-hydroxy-ethyl]sulfoximide;
S-[4-(N-{2-[N-(5-chloro(2-pyridyl))carbamoyl]-4-chlorophenyl}carbamoyl)phenyl]-S-methyl-N-(2-(diethylamino)ethyl)sulfoximide;
S-[4-(N-{2-[N-(5-chloro(2-pyridyl))carbamoyl]-4-chlorophenyl}carbamoyl)phenyl]-S-methyl-N-(2-(pyrrolidin-1-yl)ethyl)sulfoximide;
S-[4-(N-{2-[N-(5-chloro(2-pyridyl))carbamoyl]-4-chlorophenyl}carbamoyl)phenyl]-S-methyl-N-[2-dimethylamino-ethyl]sulfoximide;
S-[4-(N-{2-[N-(5-chloro(2-pyridyl))carbamoyl]-4-chlorophenyl}carbamoyl)phenyl]-S-methyl-N-[(2-(2-hydroxyethyl)-methyl-amino)-ethyl]sulfoximide;
S-[4-(N-{2-[N-(5-chloro(2-pyridyl))carbamoyl]-4-chlorophenyl}carbamoyl)phenyl]-S-methyl-N-[2-(4-methylpiperazin-1-yl)-ethyl]sulfoximide;
S-[4-(N-{2-[N-(5-chloro(2-pyridyl))carbamoyl]-4-chlorophenyl}carbamoyl)phenyl]-S-methyl-N-[2-(4-morpholinyl)-ethyl]sulfoximide;
S-[4-(N-{2-[N-(5-chloro(2-pyridyl))carbamoyl]-4-chlorophenyl}carbamoyl)phenyl]-S-methyl-N-[2-(4-methyl-homopiperazinyl)-ethyl]sulfoximide;
(−)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide;
(+)-S-[4-(N-{2-[N-(5-chloro(2-pyridyl))carbamoyl]-4-chlorophenyl}carbamoyl)phenyl]-S-methyl-N-(2-diethylamino-acetyl)sulfoximide;
S-[4-(N-{2-[N-(5-chloro(2-pyridyl))carbamoyl]-4-chlorophenyl}carbamoyl)phenyl]-S-methyl-N-(2-diethylamino-acetyl)sulfoximide hydrochloride;
S-[4-(N-{2-[N-(5-chloro(2-pyridyl))carbamoyl]-4-chlorophenyl}carbamoyl)phenyl]-S-(2-hydroxy ethyl)-sulfoximide;
S-(2-[4-(N-{2-[N-(5-chloro-2-pyridyl)carbamoyl]-4-chlorophenyl}carbamoyl)phenyl]-phenyl)-S-methyl sulfoximide;
S-(2-[4-(N-{2-[N-(5-chloro-2-pyridyl)carbamoyl]-4-chloro-6-methoxyphenyl}carbamoyl)phenyl]-phenyl)-S-methyl sulfoximide;
S-(2-[4-(N-{2-[N-(5-chloro-2-pyridyl)carbamoyl]-4-chlorophenyl}carbamoyl)phenyl]-phenyl)-S-methyl-N-acetyl sulfoximide;
S-(2-[4-(N-{2-[N-(5-chloro-2-pyridyl)carbamoyl]-4-chlorophenyl}carbamoyl)phenyl]-phenyl)-S-methyl-[N-cyclopropylcarbonyl sulfoximide;
S-(2-[4-(N-{2-[N-(5-chloro-2-pyridyl)carbamoyl]-4-chlorophenyl}carbamoyl)phenyl]-phenyl)-S-methyl-N-methoxycarbonyl sulfoximide;
S-(2-[4-(N-{2-[N-(5-chloro-2-pyridyl)carbamoyl]-4-chlorophenyl}carbamoyl)phenyl]-phenyl)-S-methyl-N-methanesulfonyl sulfoximide;
S-(2-[4-(N-{2-[N-(5-chloro-2-pyridyl)carbamoyl]-4-chlorophenyl}carbamoyl)phenyl]-phenyl)-S-methyl-N-chloroacetyl sulfoximide;
S-(2-[4-(N-{2-[N-(5-chloro-2-pyridyl)carbamoyl]-4-chlorophenyl}carbamoyl)phenyl]-phenyl)-S-methyl-N-cyano sulfoximide;
S-(2-[4-(N-{2-[N-(5-chloro-2-pyridyl)carbamoyl]-4-chlorophenyl}carbamoyl)phenyl]-phenyl)-S-methyl-N-aminocarbonyl sulfoximide;
S-(2-[4-(N-{2-[N-(5-chloro-2-pyridyl)carbamoyl]-4-chlorophenyl}carbamoyl)phenyl]-phenyl)-S-methyl-N-(4-pyridylcarbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-(4-piperidinylcarbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-(1-ethyl-piperidine-4-carbonyl)sulfoximide;
S-(2-[4-(N-{2-[N-(5-chloro-2-pyridyl)carbamoyl]-4-chlorophenyl}carbamoyl)phenyl]-phenyl)-S-methyl-N-cyanoacetyl sulfoximide;
S-(2-[4-(N-{2-[N-(5-chloro-2-pyridyl)carbamoyl]-4-chlorophenyl}carbamoyl)phenyl]-phenyl)-S-methyl-N-methoxyacetyl sulfoximide;
S-(2-[4-(N-{2-[N-(5-chloro-2-pyridyl)carbamoyl]-4-chlorophenyl}carbamoyl)phenyl]-phenyl)-S-methyl-N-(2-dimethylamino-acetyl)sulfoximide;
S-(2-[4-(N-{2-[N-(5-chloro-2-pyridyl)carbamoyl]-4-chlorophenyl}carbamoyl)phenyl]-phenyl)-S-methyl-N-(2-diethylamino-acetyl)sulfoximide;
S-(2-[4-(N-{2-[N-(5-chloro-2-pyridyl)carbamoyl]-4-chlorophenyl}carbamoyl)phenyl]-phenyl)-S-methyl-N-[2-(methyl-propyl-amino)-acetyl]sulfoximide;
S-(2-[4-(N-{2-[N-(5-chloro-2-pyridyl)carbamoyl]-4-chlorophenyl}carhamoyl)phenyl]-phenyl)-S-methyl-N-[2-(carbamoylmethyl-methyl-amino)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[(2-pyrrolidin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[(2-piperidin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(4-aminopiperidinyl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(4-methylpiperazinyl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(piperazin-1-yl)-acetyl]sulfoximide;
S-(2-[4-(N-{2-[N-(5-chloro-2-pyridyl)carbamoyl]-4-chlorophenyl}carbamoyl)phenyl]-phenyl)-S-methyl-N-[2-(imidazol-1-yl)-acetyl]sulfoximide.

11. A pharmaceutical composition which comprises compounds of formula (I), as claimed in claim 1 and a pharmaceutically acceptable carrier, diluent or excipients.

12. The compound of claim 1, wherein said compound is a factor Xa inhibitor inhibitors.

13. The compound of claim 12, wherein said compound is an anticoagulant compound suitable for humans and other warm blooded animals.

14. A medicine suitable as an anticoagulant comprising a compound of formula (I), as defined in claim 1 and a pharmaceutically acceptable carrier, diluent or excipients to a patient in need thereof.

15. Factor X inhibitors that are a compound of claim 1.

16. A method of treating a thrombosis- and/or embolism-based disease by inhibition of factor Xa, comprising the step of administering a compound of formula (I) as defined in claim 1, or a pharmaceutical composition or medicine containing said compound, to a human or animal body, to inhibit factor Xa.

* * * * *